(12) United States Patent
Hansen et al.

(10) Patent No.: US 6,228,383 B1
(45) Date of Patent: May 8, 2001

(54) USE OF FATTY ACID ESTERS AS BIOADHESIVE SUBSTANCES

(75) Inventors: Jens Hansen, Allerod; Lise Sylvest Nielsen, Copenhagen; Tomas Norling, Lyngby, all of (DK)

(73) Assignee: GS Development ab, Malmö (SE)

( * ) Notice: Subject to any disclaimer, the term of this patent is extended or adjusted under 35 U.S.C. 154(b) by 0 days.

(21) Appl. No.: 08/462,222

(22) Filed: Jun. 5, 1995

Related U.S. Application Data

(63) Continuation-in-part of application No. 08/227,526, filed on Apr. 14, 1994, now abandoned.

(30) Foreign Application Priority Data

Mar. 3, 1994  (DK) ...................................... 037/94

(51) Int. Cl.$^7$ .................................................. A61K 31/20
(52) U.S. Cl. .......................... 424/407; 514/559; 514/560; 514/558
(58) Field of Search ................................... 424/649, 407; 514/558, 559, 560

(56) References Cited

U.S. PATENT DOCUMENTS

| | | | |
|---|---|---|---|
| 5,298,258 | * | 3/1994 | Akemi et al. ......................... 424/484 |
| 5,344,655 | * | 9/1994 | Sakai et al. ........................... 424/443 |

OTHER PUBLICATIONS

Chemical Abstracts AN 1993: 11745, Honbo et al., Aug. 11, 1992.*
Chemical Abstracts AN 1992: 456, 032, Nitto et al. (1992), Mar. 9, 1992.*

* cited by examiner

Primary Examiner—Keith D. MacMillan
(74) Attorney, Agent, or Firm—Watov & Kipnes, P.C.

(57) ABSTRACT

Use of fatty acid esters as bioadhesive substances. The fatty acid esters have molecular weights below about 1000 dalton and the fatty acid component of the fatty acid ester is a saturated or unsaturated fatty acid having a total number of carbon atoms of from $C_8$ to $C_{22}$. Particularly suitable fatty acid esters for use according to the invention are fatty acid esters which are selected from the group consisting of fatty acid esters of polyhydric alcohols, fatty acid esters of hydroxycarboxylic acids, fatty acid esters of monosaccharides, fatty acid esters of glycerylphosphate derivatives, fatty acid esters of glycerylsulfate derivative, and mixtures thereof. Excellent bioadhesive properties have been observed for fatty acid esters are glyceryl monooleate, glyceryl monolinoleate or glyceryl monolinolenate. Methods are described for administering an active or protective substance to undamaged or damaged skin or mucosa of an animal such as a human by combining the active or protective substance with a bioadhesive fatty acid ester. The mucosa may be the oral, aural, nasal, lung, gastrointestinal, vaginal, or rectal mucosa. The administration may also be to body cavities such as the oral cavity, e.g. via buccal administration.

24 Claims, 6 Drawing Sheets

USE OF FATTY ACID ESTERS AS BIOADHESIVE SUBSTANCES

This application is a CIP of Ser. No. 08/227,526, filed Apr. 14, 1994, now abandoned.

The present invention relates to the use of fatty acid esters as bioadhesive substances. The fatty acid esters have molecular weights below about 1000 dalton. Furthermore, the invention relates to methods for administering an active or protective substance to undamaged or damaged skin or mucosa of an animal such as a human by combining the active or protective substance with a bioadhesive fatty acid ester. The mucosa may be the oral, aural, nasal, lung, gastrointestinal, vaginal, or rectal mucosa. The administration may also be to body cavities such as the oral cavity, e.g. via buccal administration.

BACKGROUND OF THE INVENTION

During the last decade increased attention has been given to the possibility of using bioadhesive/mucoadhesive polymers for drug delivery purposes. It is believed that several problems associated with conventional controlled release drug delivery systems may be reduced or eliminated by using a bioadhesive/mucoadhesive drug delivery system.

In conventional controlled release drug delivery systems no precautions are made in order to localize the delivery system after administration and, furthermore, the contact time in vivo between the drug delivery system and a particular site is often so short that no advantages are to be expected with respect to, e.g., modifying tissue permeability.

Compared with conventional controlled release drug delivery systems, bioadhesive drug delivery systems are believed to be beneficial with respect to the following features:
i) a bioadhesive drug delivery system localizes a drug substance in a particular region, thereby improving and enhancing the bioavailability for drug substances which may have poor bioavailability in themselves,
ii) a bioadhesive drug delivery system leads to a relatively strong interaction between a bioadhesive substance and a mucosa; such an interaction contributes to an increasing contact time between the drug delivery system and the tissue in question and permits localization of the drug delivery system to a specific site,
iii) a bioadhesive drug delivery system is contemplated to prolong delivery of drug substances in almost any non-parenteral route,
iv) a bioadhesive drug delivery system can be localized on a specific site with the purpose of local therapy e.g. treatment of local fungal diseases, permeability modification, protease and other enzyme inhibition, and/or modulation of immunologic expression,
v) a bioadhesive drug delivery system may be targeted to specific diseased tissues, and
vi) a bioadhesive drug delivery system may be employed in those cases where the conventional approach to controlled release drug delivery is unsuitable, i.e. for certain drug substances or classes of drug substances which are not adequately absorbed.

Bioadhesive substances (also denoted mucoadhesive substances) are generally known to be materials that are capable of being bound to a biological membrane and retained on that membrane for an extended period of time. Bioadhesive drug delivery systems have been the subject of a number of patent applications (see e.g. EP-A-0 516 141, WO 93/21906, and EP-A-0 581 583) but to the best of our knowledge only polymers have been regarded as bioadhesive substances. Such polymers include, e.g., acrylic acid homopolymers and copolymers, hydrophilic vinyl polymers, hydrophilic cellulose derivatives, and natural polymers.

In general, bioadhesive compositions are based on a certain content of a bioadhesive substance. As mentioned above known bioadhesive substances are polymeric substances having a molecular weight of above about 10,000. However, use of polymeric substances as bioadhesive substances in e.g. pharmaceutical compositions is limited to certain types of compositions such as, e.g., gels, i.e. compositions having a relatively high dynamic viscosity. Such a limitation is mainly due to the fact that a certain relatively high concentration of the bioadhesive substance has to be present in the composition if the composition in itself is to be bioadhesive. As mentioned above, application of a bioadhesive drug delivery system may be advantageous in many cases where application of conventional drug delivery systems is insufficient with respect to obtaining the desired effect for a predetermined period of time. However, the applicability of known bioadhesive compositions is rather limited as only relatively highly viscous compositions are bioadhesive which leaves out the possibility of e.g. having a bioadhesive sprayable composition or a bioadhesive solution of low dynamic viscosity.

DESCRIPTION OF THE DRAWING

1. Instrument probe
2. Stationary plate
3. A first holder
4. A model membrane
5. A second holder
6. Sliding stand
7. Displacement transducer
8. Control unit
9. Personal computer

1. Instrument probe
2. Stationary plate
3. A first holder
4. A model membrane
5. A second holder
6. A thermostatically controlled heater/stirrer
7. A vessel 8. Sliding stand
9. Displacement transducer
10. Control unit
11. Personal computer

DESCRIPTION OF THE INVENTION

Figure 1:
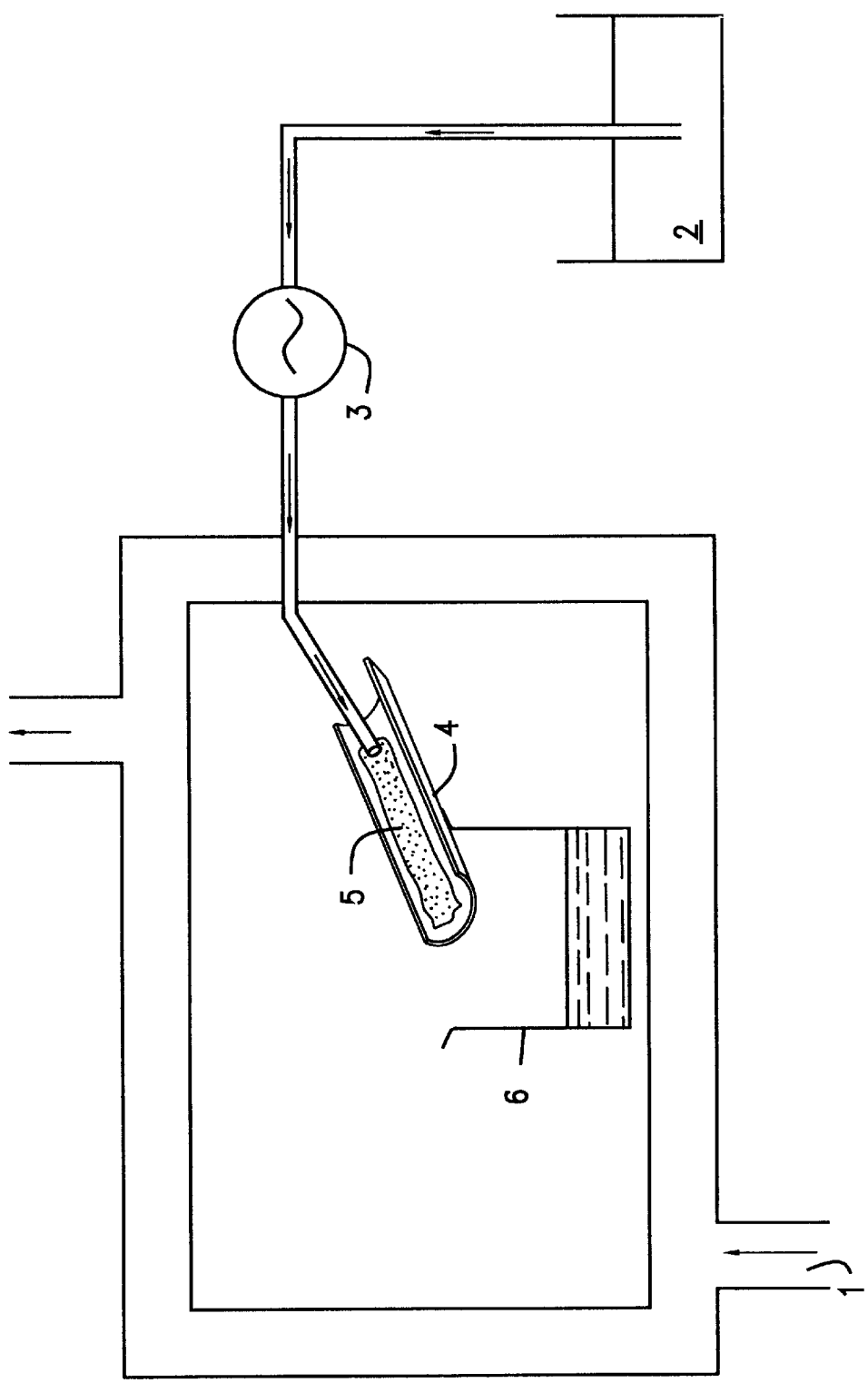
FIG. 1 shows a schematic diagram of the apparatus used in the test method denoted test method 1 described in detail in the experimental section herein. The reference numbers illustrate the following:
1. Thermostatic water flow
2. Reservoir containing the washing solution
3. A peristaltic pump
4. A stainless steel support
5. A model membrane
6. Receiver for collecting the washings

As will be apparent from the above, there is a need for identifying, developing and/or preparing bioadhesive substances which make it possible to develop bioadhesive compositions in the form of e.g. sprays, solutions, suspensions, emulsions, etc. for application to or through undamaged or damaged skin or mucosa of an animal such as a human.

The present invention meets this need by providing substances of relatively low molecular weight and with such bioadhesive properties that they impart bioadhesive properties to compositions which may be presented in the form of a spray, a solution etc. The present inventors have found that a certain class of substances has bioadhesive properties. In contrast to substances with known bioadhesive properties, the new substances are not polymers but low molecular weight compounds which have a molecular weight of at the most about 1000 dalton.

In the present context the term "a bioadhesive substance" is broadly defined as a material that is capable of being bound to a biological membrane, and retained on that membrane for an extended period of time. Accordingly, "bioadhesion" is the attachment of a material to a biological substrate such as a biological membrane. The term "a mucoadhesive substance" is in accordance with the generally accepted terminology used synonymously with the term "a bioadhesive substance". The term "mucoadhesive" underlines the fact that the adhesive bonding may be established between a material and the mucosa/mucus/mucin of a biological membrane.

The substances with hitherto unknown bioadhesive properties all belong to the class of fatty acid esters. In one aspect, the invention relates to the use of such fatty acid esters as bioadhesive substances. However, not all compounds falling under the definition of being a fatty acid ester, i.e. an ester formed by reaction of a fatty acid component (or a derivative thereof) and a hydroxy containing compound, have bioadhesive properties. For illustrative purposes it should be mentioned that the inventors have found that a combination of e.g. monoglycerides of a $C_{12}$ and $C_{18}$ fatty acid esters in a weight ratio of 1:1 is not bioadhesive according to the definition given herein. Therefore, in order to determine whether a specific fatty acid ester has bioadhesive properties and thus can be used as a bioadhesive substance in accordance with the present invention it is necessary to subject the fatty acid ester in question to a test for bioadhesiveness. Examples of suitable test methods are described in detail in the experimental section herein and definitions are given of the requirements a substance should fulfil in order to be considered as a bioadhesive substance in the present context.

Accordingly, in one aspect the invention relates to the use of a fatty acid ester which, when tested in a bioadhesive test system comprising i) placing a segment of longitudinally cut rabbit jejunum on a stainless steel support in such a manner that the mucosa layer of the jejunum is placed upside so as to allow application of said fatty acid ester, ii) placing the resulting support at an angle of 21°±2° in a cylindrical cell thermostated at 37° C.±0.5° C. and with the relative humidity kept at about 100%, iii) flushing the jejunum on the support with 0.02 M isotonic phosphate buffer solution (pH 6.5, 37° C.) for 5 min at a flow rate of 10 ml/min, iv) applying an accurately weighed amount of a sample of said fatty acid ester (about 50–150 mg such as about 100 mg) on a surface area (about 0.8×6 cm) of the mucosa of the jejunum on the support, v) dropping about 1 ml of said phosphate buffer solution on the sample applied, vi) leaving the resulting sample from step v) for 10 minutes in said cell to allow the sample to interact with glycoproteins of the jejunum, vii) flushing the jejunum with the sample applied with said phosphate buffer solution (pH 6.5, 37° C.) for 30 minutes at a flow rate of 10 ml/min, viii) collecting the washings resulting from step vii), and ix) calculating the residual amount of the sample remaining on the jejunum by measuring the amount of the sample in the washings or by measuring the amount remaining on the jejunum, results in a residual amount of at least 60% w/w such as, e.g. at least about 70% w/w, 80% w/w, 85% w/w, 90% w/w, or 95% w/w as a bioadhesive substance.

The above-mentioned test for bioadhesion is described in further details in the paragraph "Methods" under the heading "In vitro test system for bioadhesion by means of rabbit jejunum membranes". It is appreciated that the test method described above—and, accordingly, the requirements for the determination of whether a fatty acid ester is bioadhesive or not—may be replaced by other test methods such as, e.g., any one of the test methods described in the paragraph "Methods" herein.

The fatty acid esters with bioadhesive properties as evidenced by a test method such as one of the test methods described herein and which are used as bioadhesive substances according to the present invention are fatty acid esters (i.e. composed of a fatty acid component and a hydroxy-containing component) wherein the fatty acid component of the fatty acid ester is a saturated or unsaturated fatty acid having a total number of carbon atoms of from $C_8$ to $C_{22}$.

Specific examples of saturated fatty acids as components in the fatty acid esters according to the invention are selected from the group consisting of caproic acid, caprylic acid, capric acid, lauric acid, myristic acid, palmitic acid, stearic acid, arachidic acid, and behenic acid.

Specific examples of unsaturated fatty acids as components in the fatty acid esters according to the invention are selected from the group consisting of palmitoleic acid, oleic acid, linoleic acid, linolenic acid, and arachidonic acid.

Particularly suitable fatty acid esters for use according to the invention are fatty acid esters which are selected from the group consisting of fatty acid esters of polyhydric alcohols, fatty acid esters of hydroxycarboxylic acids, fatty acid esters of monosaccharides, fatty acid esters of glycerylphosphate derivatives, fatty acid esters of glycerylsulfate derivative, and mixtures thereof. In those cases where the hydroxy-containing component of the fatty acid ester is polyvalent, the hydroxy-containing component may be partially or totally esterified with a fatty acid component or with mixtures of fatty acid components.

The polyhydric alcohol component of the fatty acid ester for use according to the invention is preferably selected from the group consisting of glycerol, 1,2-propanediol, 1,3-propanediol, diacylgalactosylglycerol, diacyldigalactosylglycerol, erythritol, xylitol, adonitol, arabitol, mannitol, and sorbitol. The fatty acid esters formed from such polyhydric alcohols may be mono- or polyvalent such as, e.g., divalent, trivalent, etc. In particular fatty acid monoesters have proved to have bioadhesive properties and are therefore preferred fatty acid esters for use according to the invention. The position of the polyvalent alcohol on which the ester bond(s) is(are) established may be any possible position. In those cases where the fatty acid ester is a diester, triester etc. the fatty acid components of the fatty acid ester may be the same of different. In a most preferred aspect of the present invention, the polyhydric alcohol component is glycerol.

Examples of fatty acid esters for use according to the invention and wherein the hydroxy-containing component is a polyhydric alcohol are glyceryl monooleate, glyceryl monolinoleate, glycerol monolinolenate, and mixtures thereof. These fatty acid esters have especially promising bioadhesive properties, confer the Examples herein.

In those cases where the fatty acid ester for use according to the present invention is formed between a hydroxycarboxylic acid (or a derivative thereof) and a fatty acid (or a derivative thereof), the hydroxycarboxylic acid component of the fatty acid ester is preferably selected from the group consisting of malic acid, tartaric acid, citric acid, and lactic acid. An interesting example of a fatty acid ester for use according to the invention is a fatty acid monoester of citric acid.

As mentioned above, the hydroxy-containing component of a fatty acid ester for use according to the present invention may also be a saccharide, such as a monosaccharide such as, e.g., glucose, mannose, fructose, threose, gulose, arabinose, ribose, erythrose, lyxose, galactose, sorbose, altrose, tallose, idose, rhamnose, or allose. In those cases where the hydroxy-containing component is a monosaccharide, the fatty acid ester is preferably a fatty acid monoester of a monosaccharide selected from the group consisting of sorbose, galactose, ribose, and rhamnose.

The hydroxy-containing component of a fatty acid ester for use according to the invention may also be a glycerylphosphate derivative such as, e.g., a phospholipid selected from the group consisting of phospatidicacid, phosphatidylserine, phosphatidylethanolamine, phosphatidylcholine, phosphatidylglycerol, phosphatidylinositole, and diphosphatidylglycerol. Especially interesting compounds having a phospholipid moiety are compounds wherein the fatty acid ester is a fatty acid ester of a glycerylphosphate derivative, and the fatty acid component is selected from the group consisting of lauric acid, myristic acid, palmitic acid, stearic acid, oleic acid, linoleic acid, linolenic acid, and behenic acid. Examples of such useful fatty acid esters are dioleyol phosphatidylcholin, dilauryl phosphatidylcholin, dimyristyl phosphatidylcholin, dipalmitoyl phosphatidylcholin, distearoyl phosphatidylcholin, dibehenoyl phosphatidylcholin, dimyristyl phosphatidylethanolamine, dipalmitoyl phosphatidylethanolamine, dioleyl phosphatidylglycerol, dilauryl phosphatidylglycerol, dimyristoyl phosphatidylglycerol, dipalmitoyl phosphatidylglycerol, distearoyl phosphatidylglycerol, dipalmitoyl phosphatic acid and mixtures thereof.

Most of the fatty acid esters for use according to the invention are well-known chemical compounds which are commercially available or may be prepared by means of conventional esterification procedures involving e.g. reaction of a fatty acid derivative such as, e.g., the corresponding acid chloride with a hydroxy-containing compound (if necessary protected with suitable protection groups) and subsequently isolating the fatty acid ester, if necessary after removal of any protecting group. Many of the commercially available fatty acid esters are employed in the food industry and in general, no steps are taken in order to obtain an approximately 100% pure fatty acid ester. As an example it can be mentioned that glyceryl monooleate from Grindsted Products A/S, Denmark is a very pure product containing about 98% w/w monoesters of which more than about 80% w/w is glyceryl monooleate; the remaining monoesters are glyceryl monolinoleate, glyceryl monopalmitate and glyceryl monostearate. The fatty acid ester products for use according to the invention may thus be mixtures of fatty acid esters.

Besides the bioadhesive properties, an interesting common property has been recognized for many of the above-mentioned fatty acid esters, namely their ability to form a fluid crystalline phase upon contact with e.g. an aqueous medium. Without being limited to any theory, a presently working theory is that the ability of a specific substance to form fluid crystals and the ability of the same substance to act as a bioadhesive substance somehow are associated with each other.

The term "fluid crystalline phase" as used herein is used to denote an intermediate state between solid crystals and isotropic liquids, characterized by long-range order and short-range properties close to those of a simple liquid or solution (Keller et al., Handbook of Liquid Crystals, Verlag Chemie, Weinheim, Germany, 1980).

Examples of fatty acid esters with excellent bioadhesive properties as well as an excellent ability of forming a fluid crystalline phase are glyceryl monoesters of fatty acids. Specific examples include glyceryl monooleate (monolein) and glyceryl monolinoleate. Such fatty acid esters are capable of forming various crystalline phases upon contact with a hydrophilic medium such as water or glycerol.

Fluid crystalline phases may be a cubic (three cubic phases are known: i) the body-centered lattice, ii) the primitive diamond lattice, and iii) the gyroid), hexagonal, reverse hexagonal or lamellar phase. By the term "cubic phase" herein is meant a thermodynamically stable, viscous and optically isotropic phase made of a fatty acid ester and an aqueous medium. The terms "hexagonal phase" and "reverse hexagonal phase", respectively, are used herein to describe thermodynamically stable, viscous and optically anisotropic phases characterized by long-range order in two dimensions and made of a fatty acid ester and an aqueous medium. By the term "lamellar phase" is characterised by a long-range order in one dimension. The lamellar structure is the origin of liposomes having spherical shells of lipid bilayers. The various fluid crystalline phases can be detected and identified by use of polarized light or by means of X-ray diffraction pattern analysis (see the Examples herein).

In accordance with the above-mentioned observations, a fatty acid ester for use according to the present invention may be a fatty acid ester which is capable of forming a fluid crystalline phase on contact with an aqueous medium. The aqueous medium is a medium containing water at least in part. Apart from aqueous solutions or dispersions such a medium may be any body fluid or secretion containing water such as, e.g. in the case of a human body fluid, saliva, sweat, gastric juice, etc. The body fluid may induce formation of a fluid crystalline phase when a fatty acid ester is contacted with such a fluid.

As discussed in the Examples, a presently working theory is that the establishment of a bioadhesion between a mucosal surface and a composition comprising a fatty acid ester with bioadhesive properties is dependent on a formation of a fluid crystalline phase in situ after in situ subjecting the composition to an aqueous medium. Most likely, the formation in situ of a cubic phase is responsible for the establishment of bioadhesion. In other words, promising bioadhesive compositions within the present context are those which comprise a bioadhesive fatty acid ester which are capable of acting as a precursor for the formation of a fluid crystalline phase in situ, i.e. the compositions should be capable of forming a fluid crystalline phase after subjecting or contacting the composition to the aqueous environment at the application site.

The mechanism for bioadhesion may be rather unspecific as the fatty acid esters adhere to different types of biological tissue (e.g. buccal mucosa, gastric mucosa, intestinal mucosa, mucosa from pig and rabbit, cf. the Examples herein). It seems as if dehydration of the tissue is involved in the mechanism.

Due to the bioadhesive properties of the fatty acid esters for use according to the present invention such fatty acid esters are suitable ingredients in compositions which are formulated with the aim of obtaining bioadhesive compositions. Apart from the relevance of using bioadhesive composition within the drug delivery field (cf. the introduction herein), bioadhesive compositions are also of interest within the cosmetic, veterinary and agrochemical field. For cosmetic use according to the invention especially compositions for application on the skin are relevant. For agrochemical use according to the invention especially compositions which may adhere to cereals, corp, weeds, insects, or insect pests are important.

In pharmaceutical, cosmetic, veterinary, or agrochemical compositions the fatty acid ester for use according to the invention is generally used in a concentration of about 1% w/w to about 90% w/w or about 95% w/w, calculated on the composition. In pharmaceutical compositions the concentration of fatty acid ester(s) is preferably in a range of about 5–95% w/w such as in a concentration of at least 6% w/w such as, e.g. at least about 10% w/w, 15% w/w, 20% w/w, 25% w/w, 30% w/w, 35% w/w, 40% w/w, 45% w/w, or 50% w/w and in a concentration of at the most about 90% w/w such as, e.g., at the most 85% w/w, 80% w/w, 75% w/w, 70% w/w, 65% w/w, 60% w/w, or 55% w/w.

As mentioned above in the introduction, the viscosity of a pharmaceutical composition is an important parameter in order to determine the applicability of the composition. Use of low-molecular weight bioadhesive fatty acid esters according to the invention has made it possible to prepare bioadhesive compositions with a relatively low dynamic viscosity which indicates the potential use of such substances in formulating compositions in the form of sprays, solutions, suspension, emulsions etc. However, the use of the bioadhesive fatty acid esters according to the invention for the preparation of bioadhesive compositions is not limited to compositions of a relatively low dynamic viscosity.

In another aspect the present invention relates to the use of a bioadhesive fatty acid ester in pharmaceutical, cosmetic or agrochemical compositions, wherein the composition has a dynamic viscosity of at the most 3500 mPaS such as, e.g., at the most about 3000 mPaS, 2000 mPaS, 1500 mPaS, or 1000 mPaS, measured at a shear rate of 120 sec$^{-1}$ and at a temperature of 20° C.±0.5° C. Compositions which are intended to be presented in the form of a spray, a solution, a suspension, a dispersion, or an emulsion, or the like preferable have a dynamic viscosity of at the most 500 mPaS, such as at the most 450 mPaS, 400 mPaS, 350 mPaS, or as low as at the most 100 mPaS, measured at a shear rate of 120 sec$^{-1}$ and at a temperature of 20° C.±0.5° C. In those cases where the composition is rather solid or where the dynamic viscosity of the composition exceeds about 2000 mPaS at 20° C., it may be difficult to determine the exact dynamic viscosity at a temperature of 20° C. In these cases the dynamic viscosity may be determined at 37° C. and then the dynamic viscosity should preferably be at the most 500 mPaS, such as at the most 450 mPaS, 400 mPaS, 350 mPaS, or as low as at the most 100 mPaS, measured at a shear rate of 120 sec$^{-1}$ and at a temperature of 37° C.±0.5° C. Determination of the dynamic viscosity of a certain composition is described in the experimental section herein. The dynamic viscosity is determined on the undiluted composition.

Pharmaceutical compositions comprising a bioadhesive fatty acid ester according to the invention are intended for application to or through a nail or undamaged or damaged skin or mucosa of an animal such as a human. The mucosa is preferably selected from oral, nasal, vaginal, rectal, aural, lung, and gastrointestinal mucosa. The skin or mucosa may also be inflamed. The composition may also be administered to body cavities such as the oral cavity or by the buccal route.

Furthermore, a pharmaceutical composition comprising a bioadhesive fatty acid ester according to the invention may also be applied to a nail of an animal such as a human.

As mentioned above, the compositions comprising a bioadhesive fatty acid ester according to the invention may in themselves be bioadhesive. In a preferred aspect of the invention, the compositions are bioadhesive as evidenced by at least one of the test methods described in the experimental section herein. A bioadhesive composition comprising a bioadhesive fatty acid ester according to the invention is advantageously applied to a site such as a mucosal site at which it is subject to mechanical clearance or fluid clearance influence such as, e.g., cilia movements in the nasal cavity or saliva influence in the oral cavity etc.

Furthermore, as it is apparent form the discussion in the introduction, a composition comprising a bioadhesive fatty acid ester according to the invention may be presented in the form of a spray.

The invention also relates to the use of bioadhesive fatty acid esters in compositions which are presented in the form of a multiple unit composition.

In further aspects, the invention relates to methods for administering an active or protective substance to or through undamaged or damaged skin, mucosa or a nail of an animal such as a human comprising applying a composition which comprises the active or protective substance in combination with a fatty acid ester which, when tested in a bioadhesive test system comprising
i) placing a segment of longitudinally cut rabbit jejunum on a stainless steel support in such a manner that the mucosa layer of the jejunum is placed upside so as to allow application of said fatty acid ester,
ii) placing the resulting support at an angle of −21°±2° in a cylindrical cell thermostated at 37° C.±0.5° C. and with the relative humidity kept at about 100%,
iii) flushing the jejunum on the support with 0.02 M isotonic phosphate buffer solution (pH 6.5, 37° C.) for 5 min at a flow rate of 10 ml/min,
iv) applying an accurately weighed amount of a sample of said fatty acid ester (about 50–150 mg such as about 100 mg) on a surface area (about 0.8×6 cm) of the mucosa of the jejunum on the support,
v) dropping about 1 ml of said phosphate buffer solution on the sample applied,
vi) leaving the resulting sample from step v) for 10 minutes in said cell to allow the sample to interact with glycoproteins of the jejunum,
vii) flushing the jejunum with the sample applied with said phosphate buffer solution (pH 6.5, 37° C.) for 30 minutes at a flow rate of 10 ml/min,
viii) collecting the washings resulting from step vii), and
ix) calculating the residual amount of the sample remaining on the jejunum by measuring the amount of the sample in the washings or by measuring the amount remaining on the jejunum,
results in a residual amount of at least 60% w/w such as, e.g. at least about 70% w/w, 80% w/w, 85% w/w, or 90% w/w, the composition which comprises the active or protective substance and the fatty acid ester being such that the resulting composition in itself is bioadhesive as evidenced in that at least one of the following criteria for bioadhesion is met:
a) the composition results in a residual amount of at least 40% w/w such as at least 45% w/w, 50% w/w, or 55% w/w of the fatty acid ester or at least 40% w/w such as at least 45% w/w, 50% w/w, or 55% w/w of the active or protective substance when a sample of the composition is tested in the above-mentioned bioadhesive test system comprising steps i)–ix),
b) the composition complies with the requirement for bioadhesion defined herein when tested in a tensiometric test method such as the tensiometric method described herein,
c) the composition complies with the requirements for bioadhesion defined herein when tested for bioadhesion in an in vivo model such as the in vivo model involving testing the rinsing off ability from skin.

In the above-mentioned test, it should be noted that the requirement given under a) for the residual amount of the active or protective substance is only relevant if the active or protective substance employed has such a water solubility that a major part of the substance has not dissolved during the test.

In the present context the term "active or protective substance" is intended to mean any biologically or pharmacologically active substance or antigen-comprising material; the term includes drug substances which have utility in the treatment or prevention of diseases or disorders affecting animals or humans, or in the regulation of any animal or human physiological condition and it also includes any biologically active compound or composition which, when administered in an effective amount, has an effect on living cells or organisms.

The active substances including their physiologically and pharmaceutically acceptable salts and prodrugs which can be used according to the invention may be selected without limitation among those belonging to the following groups:

analgesic drugs such as, e.g., buprenorphine, codeine, fentanyl, morphine, hydromorphone, and the like;
anti-inflammatory drugs such as, e.g., ibuprofen, indomethacin, naproxen, diclofenac, tolfenamic acid, piroxicam, and the like;
tranquilizers such as, e.g., diazepam, droperiodol, fluspirilene, haloperidol, lorazepam, and the like;
cardiac glycosides such as, e.g., digoxin, ouabain, and the like;
narcotic antagonists such as, e.g., naloxone, nalorphine, and the like;
antiparkinsonism agents such as, e.g., bromocriptine, biperidin, benzhexol, benztropine, and the like;
antidepressants such as, e.g., imipramine, nortriptyline, pritiptylene, and the like;
antineoplastic agents and immunosuppressants such as, e.g., bleomycin, cyclosporin A, fluorouracil, mercaptopurine, methotrexate, mitomycin, and the like;
antiviral agents such as, e.g., idoxuridine, acyclovir, interferons, vidarabin, and the like;
antibiotic agents such as, e.g., clindamycin, erythromycin, fusidic acid, gentamicin, and the like;
antifungal agents such as, e.g., miconazole, ketoconazole, clotrimazole, amphotericin B, nystatin, and the like;
antimicrobial agents such as, e.g., metronidazole, tetracyclines, and the like;
appetite suppressants such as, e.g., fenfluramine, mazindol, phentermin, and the like;
antiemetics such as, e.g., metoclopramide, droperidol, haloperidol, promethazine, and the like;
antihistamines such as, e.g., chlorpheniramine, terfenadine, triprolidine, and the like;
antimigraine agents such as, e.g., dihydroergotamine, ergotamine, pizotyline, and the like;
coronary, cerebral or peripheral vasodilators such as, e.g., nifedipine, diltiazem, and the like;
antianginals such as, e.g., glyceryl nitrate, isosorbide dinitrate, molsidomine, verapamil, and the like;
calcium channel blockers such as, e.g., verapamil, nifedipine, diltiazem, nicardipine, and the like;
hormonal agents such as, e.g., estradiol, estron, estriol, polyestradiol, polyestriol, dienestrol, diethylstilbestrol, progesterone, dihydroergosterone, cyproterone, danazol, testosterone, and the like;
contraceptive agents such as, e.g., ethinyl estradiol, lynestrenol, etynodiol, norethisterone, mestranol, norgestrel, levonorgestrel, desogestrel, medroxyprogesterone, and the like;
antithrombotic agents such as, e.g., heparin, warfarin, and the like;
diuretics such as, e.g., hydrochlorothiazide, flunarizine, minoxidil, and the like;
antihypertensive agents such as, e.g., propanolol, metoprolol, clonidine, pindolol, and the like;
chemical dependency drugs such as, e.g., nicotine, methadone, and the like;
local anaesthetics such as, e.g., lidocaine, prilocaine, benzocaine, and the like;
corticosteroids such as, e.g., beclomethasone, betamethasone, clobetasol, desonide, desoxymethasone, dexamethasone, diflucortolone, flumethasone, fluocinolone acetonide, fluocinonide, hydrocortisone, methylprednisolone, triamcinolone acetonide, budesonide, halcinonide, and the like;
dermatological agents such as, e.g., nitrofurantoin, dithranol, clioquinol, hydroxyquinoline, isotretinin, methoxsalen, methotrexate, tretionin, trioxsalen, salicylic acid, penicillamine, and the like; vitamins and the like;

ophthalmic agents such as, e.g., pilocarpine, ephinefrin, timolol, atropin, and the like;

Other specific examples of active ingredients for use according to the invention are steroids such as, e.g., estradiol, progesterone, norethindrone, levonorgestrol, ethynodiol, levenorgestrel, norgestimate, gestanin, desogestrel, 3-keton-desogestrel, demegestone, promethoestrol, testosterone, spironolactone, and esters thereof, azole derivatives such as, e.g., imidazoles and mazoles and derivatives thereof, nitro compounds such as, e.g., amyl nitrates, nitroglycerine and isosorbide nitrates, amine compounds such as, e.g., pilocaine, oxyabutyninchloride, lidocaine, benzocaine, nicotine, chlorpheniramine, terfenadine, triprolidine, propanolol, metoprolol and salts thereof, oxicam derivatives such as, e.g., piroxicam, mucopolysaccharides such as, e.g., thiomucasee, opoid compounds such as, e.g., morphine and morphine-like drugs such as buprenorphine, oxymorphone, hydromorphone, levorphanol, fentanyl and fentany derivatives and analogues, prostaglandins such as, e.g., a member of the PGA, PGB, PGE, or PGF series such as, e.g., misoprostol or enaprostil, a benzamide such as, e.g., metoclopramide, scopolamine, a peptide such as, e.g., growth hormone releasing factors, growth factors (epidermal growth factor (EGF), nerve growth factor (NGF), TGF, PDGF, insulin growth factor (IGF), fibroblast growth factor (aFGF, bFGF. etc.), and the like), somatostatin, calcitonin, insulin, vasopressin, interferons, IL-2, urokinase, serratiopeptidase, superoxide dismutase (SOD), tryrotropin releasing hormone (TRH), luteinizing hormone releasing hormone (LH-RH), corticotrophin releasing hormone (CRF), growth hormone releasing hormone (GHRH), oxytocin, erythropoietin (EPO), colony stimulating factor (CSF), and the like, a xanthine such as, e.g., caffeine, theophylline, a catecholamine such as, e.g., ephedrine, salbutamol, terbutaline, a dihydropyridine such as, e.g., nifedipine, a thiazide such as, e.g., hydrochlorotiazide, flunarizine, a sydnonimine such as, e.g., molsidomine, a sulfated polysaccharide such as, e.g., heparin.

The active or protective substances mentioned above are also listed for illustrative purposes; the invention is applicable to bioadhesive compositions such as pharmaceutical and/or cosmetical compositions regardless of the active substance or substances incorporated therein.

As evidenced in the Examples herein, an active or protective substance does not significantly influence the bioadhesive properties of a vehicle provided that the concentration of the active or protective substance is relatively low such as below about 10–15% w/w or below about 8–10% w/w. The kind of active substance (structure, molecular weight, size, physicochemical properties, loading, $pK_a$ etc.) will of course be responsible for the maximal concentration which can be incorporated in the vehicle without significantly affecting the bioadhesive properties of the composition. In the Examples herein, it is also demonstrated that the active substance locates in the fluid crystalline phase of the fatty acid ester and most likely the solubility of the active substance in this phase has impact on the bioadhesive properties as well as on the release properties of the composition.

As mentioned above, the application is intended for skin or mucosa. Other applications may of course also be relevant such as, e.g., application on dentures, protheses and application to body cavities such as the oral cavity. The mucosa is preferably selected from oral, nasal, aural, lung, rectal, vaginal, and gastrointestinal mucosa.

In those cases where the method according to the invention is intended for administration of an active or protective substance to or through undamaged or damaged oral, nasal, rectal, aural or vaginal mucosa, the composition comprising the active or protective substance and the fatty acid ester may have a viscosity of at the most 3500 mPaS such as at the most 3000 mPaS, 2000 mPaS, or 1000 mPaS, measured at a shear rate of 120 $sec^{-1}$ and at a temperature of 20° C.±0.5° C. As mentioned above, the viscosity may be as low as at the most 450 mPaS especially when the composition is presented in the form of a spray, a solution, or the like. Furthermore, a bioadhesive composition for application to oral, nasal, rectal, aural or vaginal mucosa preferably contains at least 6% w/w of the fatty acid ester in the composition, calculated on the composition. Compositions for oral application in a periodontal pocket and containing glyceryl monoolein have been described in the literature, see e.g. U.S. Pat. No. 5,143,934. Compositions containing e.g. glyceryl monoolein have also been described in e.g. EP-B-0 126 751 and EP-B-0 267 617. In the latter, compositions comprising GMO/ethanol/popranolol HCl (80/15/5% w/w), GMO/ethanol/fentanyl citrate (78/20/2% w/w), GMO/ethanol/neomycin sulfate (75/20/5% w/w), GMO/ethanol/phenthermine HCl (60/30/10% w/w), and GMO/ethanol/naproxene sodium (70/20/10% w/w) are listed.

A bioadhesive composition for administration according to the invention may also be in the form of a multiple unit composition. A multiple unit composition may be administered to skin or mucosa, preferably the mucosa is selected from oral, nasal, rectal, aural, vaginal, lung, and gastrointestinal mucosa. Most preferred is a bioadhesive composition intended for administration to the gastrointestinal tract.

The individual units of the multiple unit composition for administration according to the invention comprises the fatty acid ester, e.g. in such a manner that the individual units of the composition are coated with the fatty acid ester. The individual units may also be provided with a further coating such as a film coating, or an enteric coating either in order to control the site in the gastrointestinal tract at which the active or protective substance is released or in order to control the release pattern of the active or protective substance from the composition.

The multiple unit composition may be presented in the form of a powder or in the form of a tablet or capsule, optionally provided with a coating such as a film coating, or an enteric coating.

The core of the individual units of the multiple unit composition may comprise an inert core such as a biodegradable core comprising a polysaccharide selected from the group consisting of carmelose, chitosan, pectins, xanthane gums, carrageenans, locust bean gum, acacia gum, gelatins, alginates, and dextrans, and salts thereof.

A bioadhesive composition for administration to the skin according to the invention is preferably not in the form of a plaster and has a concentration of the bioadhesive fatty acid ester of at the most 60% w/w such as at the most 55% w/w, calculated on the total weight of the composition. In EP-B-0 267 617 a fatty acid ester such as glyceryl monooleate is stated to be contained in compositions intended for application on the skin. However, the glyceryl monooleate is employed as a penetration enhancer in a concentration exceeding 60% w/w.

Bioadhesive compositions for application on skin according to the invention have generally a content of a bioadhesive fatty acid ester or mixtures of fatty acid esters of at least 6% w/w, calculated on the composition. The composition may advantageously be applied on damaged skin such as on wounds. Compositions for application to skin and especially to wounds preferably comprise a polysaccharide in a concentration of at least 15% w/w, calculated on the total weight of the composition. The polysaccharide is preferably selected from the group consisting of carmelose, chitosan, pectins, xanthane gums, carrageenans, locust bean gum, acacia gum, gelatins, alginates, and dextrans, and salts thereof. The compositions are easy to apply on the wound and are believed to be able to extract water from the wound and thereby drying the wound.

EP-B-0 126 751 describes compositions of acetylsalicylic acid and insulin, respectively, intended for administration via inhalation. The compositions are not described to be bioadhesive. The insulin composition consists of a combination of 10% w/w of a saturated solution of insulin and 90% w/w of liquid monolinolein, and the acetylsalicylic acid composition contains 80% w/w of monogalactoyl-diglyceride. Accordingly, a bioadhesive composition in the form of a spray for use according to the present invention for application to the lung mucosa does not have the above-mentioned constitution.

Apart from the active or protective substance and the bioadhesive fatty acid ester substance, the bioadhesive compositions for use according to the invention may comprise pharmaceutically or cosmetically acceptable excipients.

The bioadhesive compositions may be in form of, e.g., a spray, a solution, a dispersion, a suspension, an emulsion, tablets, capsules, pills, powders, granulates, gels including hydrogels, pastes, ointments, creams, drenches, delivery devices, suppositories, enemas, implants, aerosols, microcapsules, microspheres, nanoparticles, liposomes, and in other suitable form.

The bioadhesive compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

Pharmaceutically acceptable excipients for use in bioadhesive compositions for use according to the invention may be, for example, inert diluents or fillers, such as sucrose, sorbitol, sugar, mannitol, microcrystalline cellulose, carboxymethylcellulose sodium, methylcellulose, hydroxypropyl methylcellulose, ethylcellulose, starches including potato starch, calcium carbonate, sodium chloride, lactose, calcium phosphate, calcium sulfate or sodium phosphate;

granulating and disintegrating agents, for example, cellulose derivatives including microcrystalline cellulose, starches including potato starch, sodium starch glycolate, croscarmellose sodium, crospovidone, alginates or alginic acid;

binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, polyvinyl alcohol, or polyethylene glycol; and lubricating agents including glidants and antiadhesives, for example, magnesium stearate, zinc stearate, stearic acid, silicas, hydrogenated vegetable oils or talc.

Other pharmaceutically acceptable excipients can be colorants, flavouring agents, plasticizers, humectants, buffering agents, solubilizing agents, release modulating agents etc.

In those cases where the bioadhesive composition is in the form of a multiple unit composition, the individual units or a tablet or a capsule containing the individual units may be coated e.g. with a sugar coating, a film coating (e.g. based on hydroxypropyl methylcellulose, methylcellulose, methyl hydroxyethylcellulose, hydroxypropylcellulose, carboxymethylcellulose, acrylate copolymers (Eudragit), polyethylene glycols and/or polyvinylpyrrolidone) or an enteric coating (e.g. based on methacrylic acid copolymer (Eudragit), cellulose acetate phthalate, hydroxypropyl methylcellulose phthalate, hydroxypropyl methylcellulose acetate succinate, polyvinyl acetate phthalate, shellac and/or ethylcellulose). Furthermore, a time delay material such as, e.g., glyceryl monostearate or glyceryl distearate may be employed.

The coating may be applied on the solid dosage form in a similar manner as that described in "Aqueous film coating" by James A. Seitz in "Encyclopedia of Pharmaceutical Technology", Vol 1, pp. 337–349 edited by Swarbrick, J. & J. C. Boylan, Marcel Dekker, Inc., New York, 1988.

For application to the rectal or vaginal mucosa suitable compositions for use according to the invention include suppositories (emulsion or suspension type), solutions, enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives like, e.g., enhancers or surfactants may be incorporated.

For application to the nasal mucosa, nasal sprays and aerosols for inhalation are suitable compositions for use according to the invention. In a typically nasal formulation, the active ingredients are dissolved or dispersed in a suitable vehicle. The pharmaceutically acceptable vehicles and excipients and optionally other pharmaceutically acceptable materials present in the composition such as diluents, enhancers, flavouring agents, preservatives etc. are all selected in accordance with conventional pharmaceutical practice in a manner understood by the persons skilled in the art of formulating pharmaceuticals.

For application to the skin or nail the compositions for use according to the invention may contain conventionally non-toxic pharmaceutically acceptable carriers and excipients including microspheres and liposomes. The formulations include creams, ointments, lotions, liniments, gels, hydrogels, solutions, suspensions, sticks, sprays, and pastes. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

Examples of emulsifying agents are naturally occurring gums, e.g. gum acacia or gum tragacanth, naturally occurring phosphatides, e.g. soybean lecithin and sorbitan monooleate derivatives.

Examples of antioxidants are butylated hydroxy anisole (BHA), ascorbic acid and derivatives thereof, tocopherol and derivatives thereof, butylated hydroxy anisole and cysteine.

Examples of preservatives are parabens, such as methyl, ethyl, or propyl p-hydroxybenzoate, benzalkonium chloride, and benzylalcohol.

Examples of humectants are glycerin, propylene glycol, sorbitol and urea.

An example of a solubilizing agent (may serve as a solubilizing agent for the active or protective substance and/or for the bioadhesive fatty acid ester) is benzylalcohol.

Examples of suitable release modulating agents for use according to the invention are glycerol, sesame oil, soybean oil, lecithin and cholesterol.

Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol and Azone.

Examples of chelating agents are sodium EDTA, citric acid and phosphoric acid.

Examples of other excipients for use in compositions for use according to the invention are edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellulose, hydroxypropylcellulose, chitosane, pectin, xanthan gum, carrageenan, locust bean gum, acacia gum, gelatin, and alginates, and solvents such as, e.g., glycerol, ethanol, propylene glycol, polyethylene glycols such as PEG 200 and PEG 400, Pluronic, polysorbate, and ethylene glycol.

Examples of ointment bases are beeswax, paraffin, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

As will be understood, details and particulars concerning the method aspect of the invention will be the same as or analogous to the details and particulars concerning the use aspects discussed above, and this means that wherever appropriate, the statements above concerning the bioadhesive fatty acid esters, their preparation, improved properties and uses apply mutatis mutandis to the compositions used in the different methods for administration aspects of the invention.

The invention is further illustrated by the working examples described in the following.

Materials

Glyceryl mono-oleate (monolein), manufactured by Grindsted Products A/S, Denmark; the product used has a total content of fatty acid monoesters of at least about 96%. The product employed in the examples described herein had the following composition of fatty acid monoesters:

| | |
|---|---|
| Glyceryl monooleate | about 84% w/w |
| Glyceryl monolinoleate | about 7% w/w |
| Glyceryl monopalmitate | about 3% w/w |
| Glyceryl monostearate | about 4% w/w |

In the following Examples the term "GMO" is denoted to indicate that the above-mentioned glyceryl monooleate product is employed, i.e. a product containing at least about 84% w/w glyceryl monooleate.

Other commercially available glyceryl mono-oleate products (e.g. such as Myverol® 18-99 available from Kodak Eastman, U.S.A.) which differ in the composition of fatty acid monoesters compared with the product described above may also be applied.

Glyceryl mono-linoleate (Dimodan® LS), manufactured by Grindsted Products A/S; the product used has a total content of fatty acid monoesters of at least about 90% such as about 96% w/w. The product employed in the examples described herein had the following composition of fatty acid monoesters:

| | |
|---|---|
| Glyceryl monopalmitate | about 6% w/w |
| Glyceryl monostearate | about 6% w/w |
| Glyceryl monooleate | about 22% w/w |
| Glyceryl monolinoleate | about 63% w/w |

Other commercial available glyceryl mono-linoleate products (such as, e.g., Myverol® 18-92 available from Kodak Eastman, U.S.A.) which differ in the composition of fatty acid monoesters compared with the product described above may also be applied.

Miconazole base available from MedioLast SPA, Milano, Italy

Propranolol hydrochloride available from Sigma Chemical Co., St. Louis, U.S.A.

Lidocaine hydrochloride available from Sigma Chemical Co., St. Louis, U.S.A.

Lidocaine base available from Sigma Chemical Co., St. Louis, U.S.A.

Metoclopramid available from Sigma Chemical Co., St. Louis, U.S.A.

Isosorbid dinitrate available from Sigma Chemical Co., St. Louis, U.S.A.

Isosorbid mononitrate available from Lusochemica,

Prochlorperazin available from Diosynth

Nicotin available from Sigma Chemical Co., St. Louis, U.S.A.

Nifedipin available from Sigma Chemical Co., St. Louis, U.S.A.

Buprenorfin available from Diosynth

Acyclovir available from Heumann Pharma

Indomethacin available from Sigma Chemical Co., St. Louis, U.S.A.

Diclofenac available from Heumann Pharma

Estradiol available from Sigma Chemical Co., St. Louis, U.S.A.

Progesterone available from Sigma Chemical Co., St. Louis, U.S.A.,

Triclosan available from Ciba Geigy

Sodium fluoride available from Sigma Chemical Co., St. Louis

Tetracycline hydrochloride available from Sigma Chemical Co., St. Louis, U.S.A.

Clindamycin phosphate available from Sigma Chemical Co., St. Louis, U.S.A.

Metronidazole available from A/S Dumex, Copenhagen

Ethanol available from Danisco A/S, Denmark, complies with the DLS standard (98.8–100% w/w ethanol)

Propylene glycol available from BASF Aktiengeselschaft, Germany

Sesame oil available from Nomeco, Denmark

Soybean oil available from Nomeco, Denmark

Polysorbat 20 available from Nomeco, Denmark

Polysorbat 80 available from Nomeco, Denmark

Glycofurol available from Sigma Chemical Co., St. Louis, U.S.A.

Glycerol available from Joli Handel ApS, Denmark

Lecithin Epicuron 200 from Lucas Meyer or lecitin from Arhus Olie Fabrik

Benzyl alcohol available from Merck AG, Germany

Water, purified or distilled water

Elyzol® dental gel available from A/S Dumex

DEAE-dextran (MW=500,000) available form Sigma Chemical Co., St. Louis, U.S.A.

Sodium alginate (Sobalg FD 120) available from Grindsted Products A/S, Denmark

Hydroxypropylmethylcellulose (Methocel K15MCR Premium USP) available from Colorcon Limited, U.S.A.
Carbopol 934 available from The BFGoodrich Company, U.S.A.

Methods

Test Systems for Bioadhesion

1. In Vitro Test System for Bioadhesion by Means of Rabbit Jejunum Membranes

The test system for bioadhesion described in the following is a modified system of a method described by Ranga Rao & Buri (Int. J. Pharm. 1989, 52, 265–270).

Male albino rabbits (3–4 kg, New Zealand white rabbit SSC: CPH) was fasted for 20 hours before they were killed by means of a pentobarbital sodium injection. The intestines of the rabbits were dissected and placed in an isotonic 0.9% sodium chloride solution at room temperature (about 18° C.). Within 30 minutes the jejunums were cut and washed with 0.9% sodium chloride solution. The lumens were gently rinsed with the saline until the intestines were clean. The jejunums were cut into pieces of about 8–9 cm in length and frozen (−20° C.) immediately. The jejunums were stored up to 3 months before use (when performing the test described below it was found that the use of fresh jejunum or, alternatively, jejunum which had been frozen for up to 3 months gave reproducible and significantly similar results). Before testing, the segment of jejunum was gently thawed out.

The segment of the jejunum was cut longitudinally. It was placed on a stainless steel support (a tube of 2 cm in diameter and cut longitudinally at an axis parallel to its centre) with the mucosa layer upside, spread and held in position on the support by the adhesive effect of the jejunum itself. The support with the jejunum was placed at an angle of from about −5° to about −25° such as −7° or −21° (in the Examples the angle applied is denoted "angle" in a cylindrical cell thermostated at 37° C. A schematic description of the cell is shown in FIG. 1. The relative humidity in the thermostated cell was kept at about 100%. The jejunum was then flushed with a medium of 0.02 M isotonic phosphate buffer solution (pH 6.5, 37° C.) for 2 or 5 minutes (in the following denoted "initial rinsing period") at a flow rate of 5 or 10 ml/min (in the following denoted "initial rinsing flow"), respectively, using a peristaltic pump to equilibrate the jejunum with the buffer and to rinse off loose mucosa. An accurately weighted amount of the sample to be tested for bioadhesive properties (about 50–150 mg) was placed evenly on the mucosa of the jejunum (about 0.8×6 cm). About 1 ml of the buffer solution was carefully dropped evenly on the sample applied to ensure formation of such a fluid crystalline phase, if possible (in the case of monoolein, the fluid crystalline phase may be the cubic, hexagonal, reverse hexagonal, micellar, or lamellar phase). [In those cases where the viscosity of the test sample are relatively high or where a precipitation has taken place, the test sample is gently melted on a heating plate or in an oven at a temperature of max. 60° C. in the case of GMO or GML and cooled to a temperature of at the most about 40° C. before application on the rabbit jejunum.] Immediately after, the segments were left for 5–20 minutes such as, e.g., 10 minutes in the cell allowing the sample to interact with the glycoproteins of the jejunum and to prevent drying of the mucus. After 10 minutes, the segments were flushed evenly with the isotonic 0.02 M phosphate buffer solution (pH 6.5, 37° C.) for 15–60 minutes such as, e.g., 30 minutes at a flow rate of 5–15 ml/min such as 10 ml/min (in the Examples denoted "flow rate"). The tip of the tube carrying the buffer solution was placed 3–4 mm above the jejunum to ensure an even liquid flow over the mucosa. The washings were collected into a beaker. The amount of bioadhesive component remaining on the jejunum was calculated either by measuring the amount of sample in the beaker or by measuring the amount of sample remaining in the jejunum by means of a suitable analysis method, e.g. HPLC.

At the end of the experiment, the remaining sample on the jejunum was checked with a pair of tweezers to reveal false positive results.

In 1–2 test run out of 10 false negative results was observed probably due to a loose mucosa layer on the rabbit jejunum.

During testing and validation of the method, the parameters given above were varied (e.g. the angle applied, the flow rate, the amount applied etc.). In order to exclude false negative and false positive results it was found that the following conditions were satisfactory:

Time for prehydration before application of sample:

| | 10 min |
|---|---|
| Amount applied: | about 50–150 mg (tests have shown that a variation in the amount applied within a range of from about 25 mg to about 225 mg was without significant influence on the results obtained) |
| Angle: | −21° |
| Flow rate: | 10 ml/min |
| Flow period: | 30 minutes (it was found that a flow period of at least 10 minutes gives reproducible results and a prolongation of the period to about 50 minutes does not significantly change the result) |

Furthermore, it was found advantageous that the method allows rinsing of the sample applied on the jejunum by an aqueous medium, thus allowing a fluid crystalline phase to be formed. The method also permits application of fluid samples and pellets.

Determination of the Bioadhesiveness of a Test Sample

In those cases where the test sample is a fatty acid ester, the fatty acid ester is considered as bioadhesive if the residual amount is at least about 60% w/w such as at least about 65% w/w, about 70% w/w, about 75% w/w, about 80% w/w, about 85% w/w, 90% w/w, or about 95% w/w.

In those cases where the test sample is a composition comprising a combination of a fatty acid ester and an active or protective substance, the composition is considered bioadhesive if the residual amount (of fatty acid ester or active/protective substance) is at least about 40% w/w such as at least about 45% w/w, about 50% w/w, 55% w/w, 60% w/w, 65% w/w, 70% w/w, 75% w/w, or 80% w/w.

In the present context evaluation of the bioadhesive properties of a substance may also be performed by use of the test system and test conditions described above but modified with respect to type of membrane, amount applied of test sample, test angle, flow rate, medium, etc. In this connection, tests have been performed in order to evaluate the influence of different membranes on the test results. The following results were obtained using the above-mentioned test conditions (angle: −21°, flow rate: 10 ml/min, and flow period: 30 min) and applying GMO on the membrane:

| Membrane % w/w | Bioadhesion Residual amount % |
|---|---|
| rabbit jejunum | 90 |
| pig ileum | 106* |
| pig stomach | 106* |
| buccal pig mucosa | 88 |

*the high result is most likely due to an interference from the intestines or the stomach 2. In Vitro Test System for Bioadhesion by Means of Tensiometry The test system for bioadhesion described in the following is a modified system of a method described by Tobyn, M., J. Johnson & S. Gibson (in "Use of a TA.XT2 Texture Analyser in Mucoadhesive Research", International LABMATE, 1992, XVII (issue VI), 35–38).

The test system involves measuring the tensile force required to break an adhesive bond formed between a model membrane and a test sample (i.e. the sample which is tested for its bioadhesive properties).

Figure 2A:
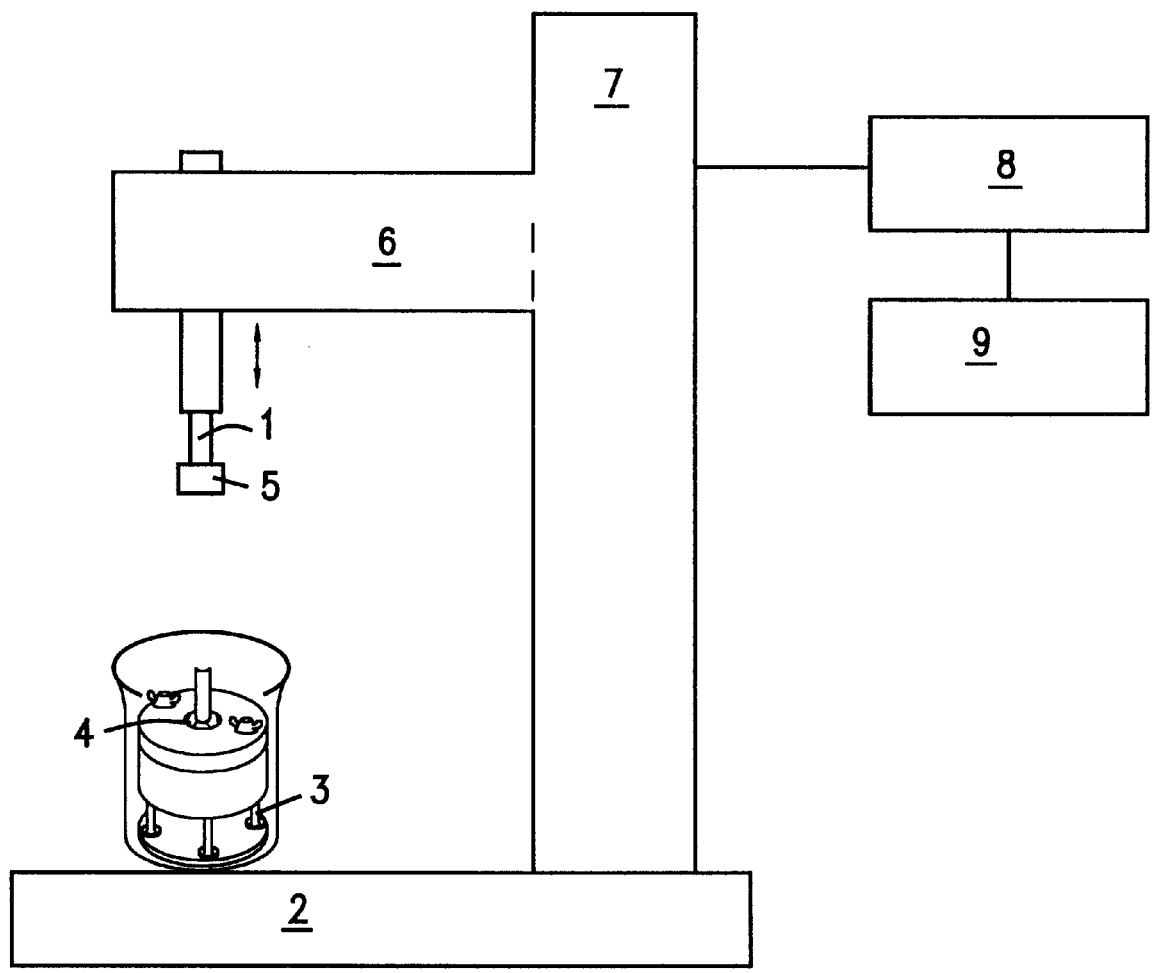
FIG. 2A shows a schematic diagram of the apparatus used in the test method denoted test method 2 described in detail in the experimental section herein. The reference numbers illustrate the following.
Figure 2B:
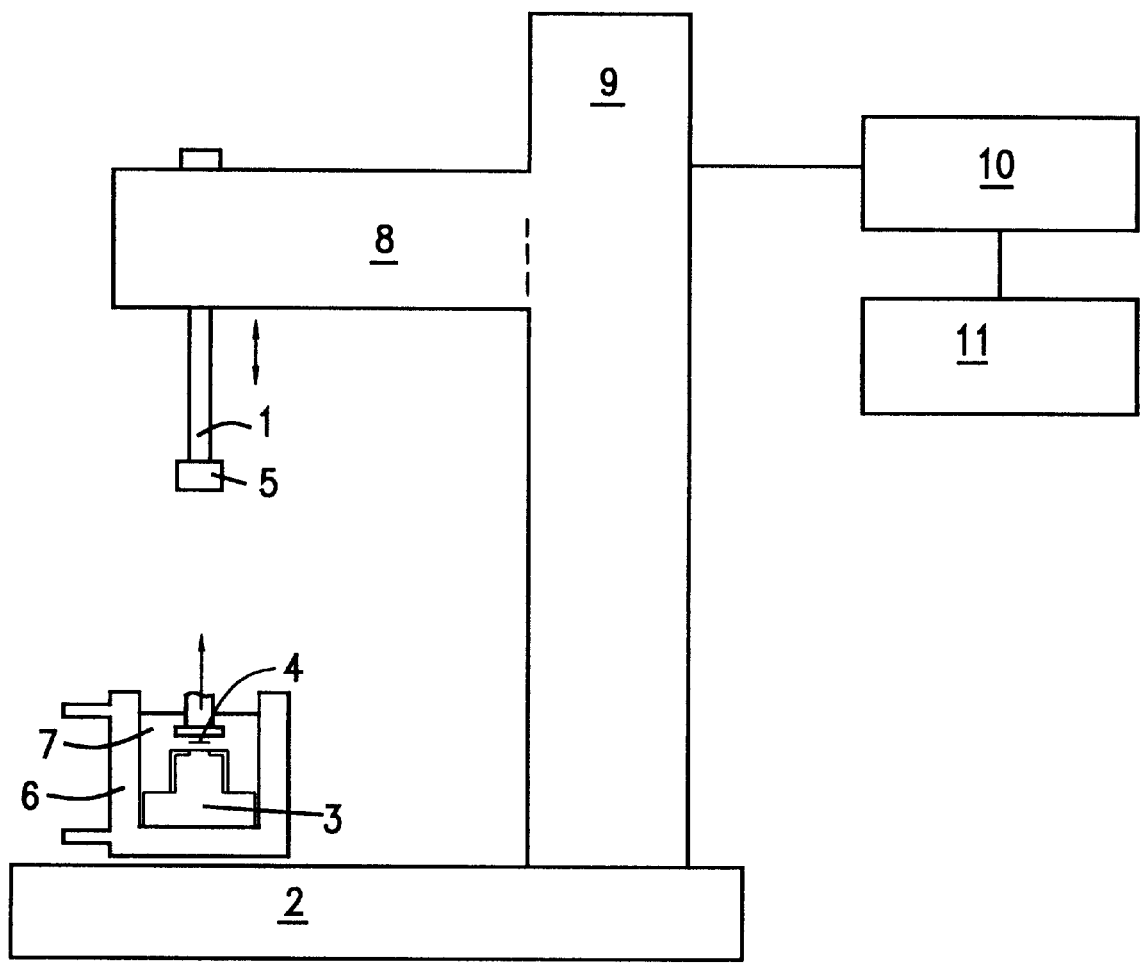
FIG. 2B shows a schematic diagram of a variation of the apparatus used in the test method denoted test method 2 described in detail in the experimental section herein. The reference numbers illustrate the following.

The test apparatus employed in the following is a TA.XT2 Texture analyser (Stable Micro System Ltd., Haslemere, UK) (FIG. 2) equipped with a 5 kg load cell interfaced with an IBM PC computer running XT-RA dimension software, DOS version. The test enables measuring the strength of adhesive bonding established by contacting a model membrane, i.e. in this case a pig intestine segment, and the test sample. An analogous test apparatus may also be employed.

The TA.XT2 Texture analyser apparatus is equipped with an instrument probe 1 (see FIG. 2) which is movable in a vertical direction at a variable rate. During the so-called withdrawal phase of the testing, the instrument probe is moved upwards with a constant rate until detachment occurs (see below). Furthermore, the apparatus is equipped with a stationary plate 2 on which a first holder 3 is placed. Before and during a test run, a model membrane 4 is fixed on this holder, e.g. by means of a cap or double adhesive tape or glue. The area exposed to the test may be determined by the area of the probe (preferred in this case) or by the area of the test samples (e.g. a coated cover glass), or by the area of a holder fixed to the probe. The accurate size of the exposed area is used in the calculation of the adhesive strength (see below).

As mentioned above, the test involves employment of a model membrane, primarily of animal origin. The membrane could be e.g. rabbit, rat or pig gastric mucosa; a segment of rabbit, rat or pig intestines, e.g. a segment of rabbit jejunum; a segment of rabbit or porcine buccal mucosa; or a segment of rabbit, rat or pig intestines from which the mucosal layer has been removed prior to testing; or skin from an animal (after removal of substantially all subcutaneous fat); or it could be artificial or commercial available mucin.

In the tests described below, duodenum, jejunum and the upper part of ileum from freshly slaughtered pigs were used. The gut was stored on ice until it was washed with 0.9% w/w sodium chloride solution within 2 hours. The lumens were gently rinsed with the saline until the intestines were clean. The gut was cut into pieces of 3–4 cm and immediately frozen (−20° C.). The intestines were stored up to 2 months before use. Before testing, the segments were gently thawed out. The gut segment was opened along the mesenteric border. Serosa and muscularis layers were removed by stripping with a pair of tweezers, taking care to maintain the integrity of the mucus layer. This resulted in a flattening of the originally folded mucosal surface. Before use the tissue was equilibrated in the testing medium for about 10 min, which was sufficient for the tissue to attain temperature and pH equilibrium as measured by pH paper.

If the results obtained by use of another membrane than the one mentioned above to compare the bioadhesive properties of various substances or combinations, the results of a reference compound could be included. As discussed below testing of a reference sample may also be made as a routine. Polycarbophil and Carbopol 934 have been found suitable as reference compounds.

An accurate amount of a test sample (about 25–500 mg) is applied in a uniform layer either i) on the luminal side of the model membrane placed on the first holder, ii) directly on the instrument probe, if necessary by means of a cap, a double adhesive tape or glue applied on the instrument probe before application of the test sample, iii) on a cover glass which is placed on the instrument probe with the test sample pointing downwards, or iv) via a probe modified in such a manner that it allows application of a relatively low viscous or semi-solid sample, the modified probe allows also the necessary addition of an aqueous medium.

In those cases where it is not possible to fix the test sample to the instrument probe, the apparatus may be equipped with a second holder 5 on which another model membrane is fixed. In such cases, the model membranes employed on the two holders are usually of the same type. It is also possible to fix the other model membrane directly to the instrument probe e.g. by means of a double adhesive tape, glue, or a cap.

For an adhesion test a tissue (porcine intestinal mucosa) of about 3×3 cm was fixed on the tissue holder 3 with the mucosa layer upside. Before application of the tissue, a piece of gauze was placed directly on the tissue holder, and thereupon the tissue was placed. This precaution is made in order to stabilize the contact force. In order to moist the tissue and hydrate the sample, about 0.5 ml isotonic 0.05 M phosphate buffer, pH 6.0 was added to the tissue. Such an addition also enables a cubic phase to be formed. The instrument probe with ample (see below) was lowered with a test speed of 0.1 m/sec in order to bring the tissue and the sample in contact under a constant force. The contact area was either 1.33 $cm^2$ (cover glass) or 1.27 $cm^2$ (probe) depending on the method of sample preparation. The contact force was set to 0.2 N and the contact time was 30 min. After 30 min the probe was withdrawn with a rate of 0.1 mm/sec (post test speed) for 10 mm. Initial experiments showed that this distance was well beyond the point where the sample and mucous separated during withdrawal.

The peak detachment force and the area under the force/time curve was calculated automatically using the XT-RA dimension software. The work of adhesion (mJ $cm^{-2}$), said to be the most accurate predictor of mucoadhesive performance, was calculated.

Sample Preparation

Application method of the polymers used as reference:

Cover glasses having a diameter of 13 mm (area 1.33 $cm^2$) were coated with the polymers under investigation by pipetting 100 μl of a 1% w/w solution of methanol or water in the center of the glass plate. After drying for 2 hours at 60° C. in an oven, a thin polymer film remained. One cover glass was attached to the probe (diameter of 12.7 mm) with its non-coated side by means of doble adhesive tape.

Cover glasses and mucosa were only used once (i.e. for one measurement)

Application of fatty acid ester compositions:
A. Melting (if possible) of the solid or semi-solid composition and dipping the probe into it (this method is only used it the melting procedure does not change the properties of the composition) The sample (25–100 mg) was applied to the probe in a smooth layer by dipping the probe into melted GMO. The sample was solidified at room temperature or, if necessary by cooling.
B. Smearing 25–100 mg of the sample directly on the probe.
C. Fixing the sample by means of a cap, double adhesive tape or glue Test runs are performed after the tissue has equilibrated in an aqueous medium at room temperature for 5–20 min. Then the tissue was removed from the aqueous medium and placed in the test apparatus and then the test was run.

In some cases, variations of the above-given method may be relevant, e.g. running the test in an aqueous medium or running the test at a temperature different from room temperature such as 37° C.

Furthermore, the test parameters may be varied, e.g. as follows:

| | |
|---|---|
| Hydration time: | 0–20 min |
| Contact time: | 60 sec–50 min |
| Contact force: | 0.05–0.4 N |
| Equilibration medium | |
| Test speed: | 0.02–1 mm/sec |
| Post test speed: | 0.02–1 mm/sec |

Test run temperature may be changed by employing a suitable temperature controlled oven such as a SMTC/04 from Stable Microsystems, Haslemere, UK.

Determination of the Bioadhesive Properties of a Test Sample

In order to test whether a test sample is bioadhesive, two test runs are performed:
1. A test run with the test sample applied (result: work of adhesion $WA_S$)
2. A test run with a known and excellent bioadhesive sample (e.g. polycarbophil) (result: work of adhesion $WA_R$)

In both cases the work of adhesion is calculated and the test sample is considered bioadhesive if $WA_S/WA_R \times 100\%$ is at least 30%, such as 35%, 40%, 45%, 50%, or 55%. In general, a sample is graded to be a week bioadhesive if the result is less than about 30%, a medium bioadhesive if the result is about 30%–50%, a strong bioadhesive if the result is at least 50%.

Polycarbophil (Noveon™ AA-1, BF Goodrich, Hounslow, U.K.) is a high molecular weight poly(acrylic acid)copolymer loosely cross-linked with divinyl glycol. On account of its known excellent mucoadhesive properties, this polymer serves as a reference. Before testing in the above-mentioned tensiometric test, a polycarbophil gel is prepared by mixing polycarbophil with water or methanol (resulting concentration about 10–20 mg ml$^{-1}$) and the mixture is allowed to hydrate at room temperature for 24 hours. The polymer solution is periodically stirred. The resulting gel is applied on a cover glass and tested as described above and the result obtained is used as a reference value for excellent bioadhesive substances.

Similarly, other substances which are known bioadhesive substances are tested such as, e.g., chitosane, tragacanth, hydroxypropylmethylcellulose (HPMC), sodium alginate, hydroxypropylcellulose (HPC), karaya gum, carboxymethylcellulose (CMC), gelatin, pectin, acacia, PEG 6000, povidone, or DEAE-dextran (less bioadhesive than polycarbophil). By choosing test substances with various degrees of bioadhesiveness an evaluation scale can be made and the performance of a test sample with respect to bioadhesiveness can be evaluated. It is contemplated that the following scale is applicable provided the test conditions given above is applied. It is clear that if the test conditions are changed, another scale may be more relevant. A suitable scale is then to be based on the values obtained for the excellent bioadhesive polycarbophil and the week bioadhesive such as, DEAE-dextran.

| Bioadhesive properties | Work of adhesion (mJ cm$^{-2}$) |
|---|---|
| none | less than 0.005 |
| poor | about 0.005–about 0.012 |
| moderate | about 0.012–about 0.020 |
| good | about 0.020–about 0.04 |
| excellent | more than 0.04 |

When testing some known bioadhesive substances and GMO, the following results were obtained as a mean of six experiments:

| Test substance | Work of adhesion (mJ cm$^{-2}$) |
|---|---|
| DEAE-dextran | 0.010 |
| Sodium alginate | 0.015 |
| GMO/water 85/15% w/w* | 0.028 |
| HPMC | 0.036 |
| Carbopol 934 | 0.031 |
| GMO | 0.047 |
| Polycarbophil | 0.060 |

*: lamellar phase

3. In Vivo Test System for Bioadhesion—Washing Off Ability from the Skin

A water soluble dye (Edicol Sunset Yellow, E 110, Amaranth E-123, or Brilliant Blue E 131) and/or a lipid soluble dye (Waxoline violet A FW (Maximex), Colur flavus insolubilis, DAK 63, or Edilake tartrazin NS) was added to the test sample and mixed to form a homogeneous mixture. In those cases where a water soluble dye was used, the dye was preferably dissolved in an aqueous medium before mixing. About 0.05–0.5 g of the resulting mixture was applied in a uniform layer on an area of about 4 cm$^2$ of the skin of the hand or of the wrist. The test samples could be applied on dry skin as well as on moistened skin. In some cases, about 5 min before running the test, a small amount of water could be added to the test sample applied. Immediately after application, the test sample on the skin was subjected to washings with water from a tip (flow rate corresponding to about 6–8 liters/minutes and a temperature of about 35–40° C.). The washings were carried out for about 3 minutes. Then it is visually assessed in which degree the test sample is retained on the skin. The visual assessment is done by use of a scale graded from 1–5, where 5 represents total retainment of the test sample applied on the skin and 1 represents no retainment of the test sample on the skin.

The test sample is evaluated to have bioadhesive properties in the present context if the result of the above-described test is at least a 4.

The test described above has proved to be suitable when testing compositions for bioadhesiveness and the compositions in question have a relatively high viscosity which makes it difficult to apply the compositions to the rabbit jejunum model.

Determination of Viscosity

The dynamic viscosity of a test sample or a composition is determined using a RheoStress RS 100 Rheometer, HAAKE (Germany) equipped with a RS 100 1.2 software package. The measurement is performed at 20° C.±0.5° C. or, alternatively, at 37° C.±0.5° C. using the following conditions: probe: plate (d=20 mm), gab: 0.5 mm, shear rate: 120 sec$^{-1}$, time: 300 sec. The viscosities are read at time t=180 sec.

Quantitative Determinations of Glyceryl Mono-Oleate and Glyceryl Mono-Linoleate by Means of HPLC The quantitative determination of glyceryl mono-oleate or glyceryl mono-linoleate was made by high-performance liquid chromatography (HPLC) using a Shimadzu LC-6A HPLC pump, a Shimadzu SPD-6A UV detector, a Shimadzu C-5A integrator and a Shimadzu SIL-6B autosampler.

The column (25 cm×4 mm i.d.) was packed with Supelcosil LC-18-DM and was eluted isocratically at ambient temperature with a mobile phase consisting of methanol-:water:acetate buffer (pH 3.5) (840:120:40 v/v). However, in some cases interference from other substance may occur and then it may be necessary to make minor changes in the composition of the eluent.

The size of a sample injected on the column was 20 μl and the flow rate was 1.2 ml/ml. The column effluent was monitored at 214 nm.

Extraction Procedure Prior to Analysis of Glyceryl Mono-Oleate or Glyceryl Mono-Linoleate in Mucosa The mucosa in question (with a fatty acid ester, e.g. glyceryl mono-oleate) is placed in 50.00 ml of methanol and shaken for 2 hours. The mixture is filtered through a 0.45 μm filter membrane (from Millipore 16555Q) and the filtrate is subjected to HPLC analysis using the method described above.

Recovery

In those cases where analysis is performed in order to determine the residual amount of fatty acid ester (e.g. glyceryl mono-oleate) on the rabbit jejunum segment in connection with the bioadhesive test No. 1 (above), the calculation of the residual amount takes into consideration an appropriate correction in the recovery. This correction is found based on determination of the amount of fatty acid ester on the rabbit jejunum segment after application of an accurate amount of fatty acid ester (this test is repeated 5 times and the recovery is given as the mean value).

The recovery of about 125 mg GMO/ethanol 60/40% w/w on rabbit jejunum was examined. The recovery was found to be about 90%. The recovery was not determined for the other amounts of GMO/ethanol 60/40% w/w nor was it determined for GMO or GML formulations to which drug substances or excipients were added.

EXAMPLES

The following examples 1–13 relate to the preparation of bioadhesive compositions or bioadhesive vehicles for use according to the present invention.

Unless otherwise stated, all percentages are by weight.

In all examples, the glyceryl mono-oleate (abbreviated as GMO in the following) (and whenever relevant Dimodan® LS) is gently melted on a heating plate or in an oven and the liquid obtained (max. temperature of the melted liquid is about 60° C.) is cooled to about 40° C. before mixing with other ingredients. The monoglyceride mixtures and the ingredients were mixed by stirring or shaking. In those cases where the composition contains an active substance in a GMO/ethanol or GML/ethanol vehicle, one of the following methods was applied:

1. The active substance was dissolved or dispersed in ethanol and then mixed with melted GMO under stirring
2. The active substance was dissolved or dispersed in melted GMO and then ethanol was added under stirring
3. The active substance was dissolved or dispersed in a GMO/ethanol mixture.

When storing at room temperature (22° C.) some formulations become inhomogeneous. In relevant cases the formulations were melted and stirred to obtain a homogeneous mixture before use.

In those cases where a bioadhesive test is performed, the values given are mean values of the results of 2–4 tests. It should be noted that the values given in the Examples are not corrected for recovery, i.e. the values are minimum values. If a correction for recovery is made the values with become larger.

In the following examples 1–13 the test conditions for performing Test No. 1 for bioadhesiveness were:

| | |
|---|---|
| angle: | −7° |
| initial rinsing period: | 2 minutes |
| initial rinsing flow: | 5 ml/min |
| flow rate: | 5 ml/min |
| flow period: | 30 minutes |

In the following examples 14–21 the test conditions for performing Test No. 1 for bioadhesiveness were:

| | |
|---|---|
| angle: | −21° |
| initial rinsing period: | 5 minutes |
| initial rinsing flow: | 10 ml/min |
| flow rate: | 10 ml/min |
| flow period: | 30 minutes |

Example 1

Preparation of a Sprayable Composition Containing Licocaine Hydrochloride as Active Substance The compositions 1A and 1B, respectively, were prepared from the following ingredients:

| | 1A | 1B |
|---|---|---|
| GMO | 48 g | 57 g |
| Ethanol | 32 g | 38 g |
| Lidocaine hydrochloride | 20 g | 5 g |

The GMO was mixed with ethanol and lidocaine hydrochloride was added to the mixture while stirring.

The compositions were tested for bioadhesiveness in test system No. 1. A residual amount of about 71% w/w and 84% w/w GMO for compositions 1A and 1B, respectively, was found after testing.

Example 2

Preparation of a Semi-Solid (Colourless Gel) Composition Without any Active Substance The composition was prepared from the following ingredients:

| | |
|---|---|
| GMO | 65 g |
| Water | 35 g |

The GMO and water were mixed by shaking. The liquid crystal structure of the gel obtained is cubic as evidenced by polarized light.

The composition was tested for bioadhesiveness in test system No. 3 (washing off ability). A score of 4–5 was found indicating that the composition is bioadhesive.

Example 3
Preparation of a Semi-Solid Composition Without an Active Substance The composition was prepared from the following ingredients:

| | |
|---|---|
| GMO | 85 g |
| Water | 15 g |

The GMO and water were mixed by shaking and a lamellar phase of GMO was obtained as evidenced by polarized light.

The composition was tested for bioadhesiveness in test system No. 1. A residual amount of about 84% w/w GMO was found after testing.

The composition was also tested for bioadhesiveness in test system No. 3 (washing off ability). A score of 4 was found indicating that the composition is bioadhesive.

Example 4
Preparation of a Sprayable Composition Containing Water

The composition was prepared from the following ingredients:

| | |
|---|---|
| GMO | 50 g |
| Ethanol | 40 g |
| Water | 10 g |

The GMO was added to a mixture of ethanol and water. The mixture was finally shaken vigorously.

Example 5
Preparation of a Semi-Solid Composition (Colourless Gel) Without an Active Substance The composition was prepared from the following ingredients:

| | |
|---|---|
| GMO | 65 g |
| Glycerol | 35 g |

The GMO and glycerol were mixed by shaking.

The liquid crystal structure of the gel obtained is cubic as evidenced by polarized light.

The composition was tested for bioadhesiveness in test system No. 3 (washing off ability). A score of 4–5 was found indicating that the composition is bioadhesive.

Example 6
Preparation of a Liquid Composition Without an Active Substance

The composition was prepared from the following ingredients:

| | |
|---|---|
| GMO | 50 g |
| Ethanol | 30 g |
| Glycerol | 20 g |

The GMO was mixed with ethanol and glycerol was added to the resulting mixture while stirring.

The composition was tested for bioadhesiveness in test system No. 1. A residual amount of about 81% w/w GMO was found after testing.

Example 7
Preparation of a Liquid Composition Without an Active Substance

The composition was prepared from the following ingredients:

| | |
|---|---|
| GMO | 60 g |
| Ethanol | 30 g |
| Benzyl alcohol | 10 g |

The GMO was mixed with ethanol and benzyl alcohol was added to the resulting mixture while stirring.

The composition was tested for bioadhesiveness in test system No. 1. A residual amount of about 87% w/w GMO was found after testing.

Example 8
Preparation of a Semi-Solid Composition Without an Active Substance The composition was prepared from the following ingredients:

| | |
|---|---|
| Dimodan ® LS | 65 g |
| Water | 35 g |

Water was added to the Dimodan® LS under vigorous stirring.

The composition was tested for bioadhesiveness in test system No. 3 (washing off ability). A score of 4–5 was found indicating that the composition is bioadhesive.

Example 9
Preparation of a Sprayable Composition Without an Active Substance The composition was prepared from the following ingredients:

| | |
|---|---|
| Dimodan ® LS | 60 g |
| Ethanol | 40 g |

Ethanol was added to Dimodan® LS and mixed.

The composition was tested for bioadhesiveness in test system No. 1. A residual amount of about 95% w/w GMO was found after testing.

Example 10
Preparation of GMO-Containing Pellets (Corresponding to 11% w/w GMO)

An inert core having a particle size of about 100–200 μm was coated with two different film forming materials. The inner coat was Surelease (Colorcon) which is an aqueous dispersion of colloidal ethylcellulose with a plasticizer. The outer coat was GMO which was applied as a 80% solution in ethanol.

The composition was tested for bioadhesiveness in test system No. 1. The amount applied was 55 mg of pellets. A residual amount of about 72% w/w GMO was found after testing.

Example 11
Preparation of GMO-Containing Pellets (Corresponding to 18% w/w GMO)

An inert core having a particle size of about 100–200 μm was coated with two different film forming materials. The inner coat was Surelease (Colorcon) which is an aqueous dispersion of colloidal ethylcellulose with a plasticizer. The outer coat was GMO which was applied as a 80% solution in ethanol.

The composition was tested for bioadhesiveness in test system No. 1. The amount applied was 55 mg of pellets. A residual amount of about 68% w/w GMO was found after testing.

Example 12
Preparation of a Sprayable Composition Without an Active Substance

The composition was prepared from the following ingredients:

| | |
|---|---|
| GMO | 60 g |
| Ethanol | 40 g |

Ethanol was added to GMO and mixed.

The composition was tested for bioadhesiveness in test system No. 1. A residual amount of about 81% w/w GMO was found after testing.

Example 13
Preparation of a Sprayable Composition Without an Active Substance

The composition was prepared from the following ingredients:

| | |
|---|---|
| GMO | 60 g |
| Ethanol | 40 g |

Ethanol was added to the GMO and mixed.

The composition was tested for bioadhesiveness in test system No. 1. The test system was modified in that a segment of rabbit jejunum was employed in which the mucus layer has been removed. A residual amount of about 82% w/w GMO was found after testing.

Example 14
Investigation of the Influence of the Concentration of the Active Substance on the Bioadhesiveness Compositions were prepared by adding to a solution of GMO/ethanol 60/40% w/w or to a solution of GML/ethanol 60/40 w/w, respectively, different amounts of miconazole. In the table given below, results are given with respect to bioadhesiveness after testing of the compositions in test system No. 1.

| Concentration of miconazole (% w/w) | Bioadhesion (residual amount %) | | | |
|---|---|---|---|---|
| | GMO-based | | GML-based | |
| | I* | II** | I* | II** |
| 0 | | 85 | 96 | 95 |
| 2 | 88 | | 98 | |
| 3 | 87 | | | |
| 4 | 87 | 72 | 84 | 86 |
| 5 | 89 | | | 41 |
| 6 | 61 | 72 | 88 | |
| 8 | 21 | 33 | 90 | |
| 10 | | | 30 | 4 |
| 15 | 12 | | 12 | |
| 25 | 1 | | | |

I*: the tests was run employed the following test conditions: initial rinsing period: 2 min, initial rinsing flow: 5 ml/min, angle: −7°, flow rate: 5 ml/min, flow period: 30 min
II*: the tests was run employed the following test conditions: initial rinsing period: 5 min, initial rinsing flow: 10 ml/min, angle: −21°, flow rate: 10 ml/min, flow period: 30 min The results show that compositions containing miconazole in concentrations up to about 6–8% w/w are bioadhesive. A high concentration of drug substance in a composition seems to influence the bioadhesiveness in a negative direction.

In many cases it has been found that the active substance is dissolved in the cubic phase. When the solubility of the active substance in the cubic phase is exceeded, the cubic phase structure is disturbed and another fluid crystalline phase may be formed. The results given above indicate that the cubic phase of GMO and GML is the most bioadhesive crystalline phase when formed in situ.

Example 15
Preparation of a Bioadhesive Composition Comprising Metoclopramide as an Active Substance Compositions comprising various concentrations of metoclopramide were prepared by adding an appropriate amount of metoclopramide to a solution of GMO/ethanol 60/40% w/w and subsequently stirring the mixture. The compositions were tested for their bioadhesive properties by subjecting them to test system No. 1. The results are described below:

| Concentration of metoclopramide % w/w | Bioadhesion Residual amount % |
|---|---|
| 1 | 81 |
| 3 | 77 |
| 5 | 70 |

The results show that compositions based on GMO/ethanol 60/40% w/w containing at least 5% w/w metoclopramide are bioadhesive.

Example 16
Preparation of Bioadhesive Compositions Containing Isosorbide Dinitrate The compositions were mainly prepared as described in Example 15 above with the exception that isosorbide dinitrate was used instead of metoclopramide. However, isosorbide dinitrate is only available in admixture with lactose. Therefore, the preparation of the composition involved the filtration of the in ethanol slightly soluble lactose from a mixture of isosorbide dinitrate/lactose and ethanol (isosorbide dinitrate is freely soluble in ethanol). When lactose was filtered off melted GMO was added under stirring. The results of the bioadhesiveness of the composition employing test system No. 1 are given below and show the same picture as the one obtained in Example 15, namely that compositions which are based on a bioadhesive mixture (e.g. a mixture of GMO and ethanol) maintain their bioadhesiveness even if a drug substance like, e.g. isosorbid dinitrate is added in a concentration of at least 5% w/w.

| Concentration of isosorbide dinitrate % w/w | Bioadhesion Residual amount % |
|---|---|
| 2 | 85 |
| 5 | 88 |

Example 17

Testing of Compositions Based on Bioadhesive Vehicles and Containing an Active Drug Substance Compositions containing various concentrations of different active drug substances were prepared using the general method. The compositions prepared are based on mixtures of GMO and ethanol in concentrations which have proved to be bioadhesive in themselves. The compositions containing an active drug substance were tested for bioadhesiveness using test system No. 1. The results are given below:

| Composition % w/w | Bioadhesion Residual amount % |
|---|---|
| GMO/ethanol/nicotin: | |
| 59.7/39.8/0.5 | 87 |
| 59.4/39.6/1 | 89 |
| 58.8/39.2/2 | 92 |
| GMO/ethanol/water/nicotin | |
| 49/39.2/9.8/2 | 83 |
| GMO/ethanol/dichlorphenac: | |
| 58.8/39.2/2 | 74 |
| 57/38/5 | 11 |
| 54/36/10 | 0 |
| GMO/ethanol/lidocain HCl/lidocain base: | |
| 57/38/5/0 | 83 |
| 54/36/10/0 | 61 |
| 57/38/0/5 | 89 |
| 54/36/0/10 | 21 |
| 57/38.2/2.5/2.5 | 84 |
| 54/36/5/5 | 78 |
| GMO/ethanol/burprenorfin: | |
| 59.4/39/6/1 | 85 |
| 58.8/39.2/2 | 71 |
| GMO/ethanol/estradiol: | |
| 59.4/39.6/1 | 87* |
| 58.2/38.8/3 | 77 |
| GMO/ethanol/progesterone: | |
| 59.4/39.6/1 | 104 |
| 58.2/38.8/3 | 103 |
| 57/38/5 | 98 |
| GMO/ethanol/indomethacin: | |
| 58.2/38.8/2 | 91 |
| 57/38/5 | 98 |
| 54/36/10 | 25 |

-continued

| Composition % w/w | Bioadhesion Residual amount % |
|---|---|
| GMO/ethanol/nifedipine: | |
| 58.2/38.8/2 | 94 |
| GMO/ethanol/triclosan: | |
| 59.4/39.6/1 | 101 |
| 58.2/38.8/3 | 109 |
| 57/38/5 | 105 |
| GMO/acyclovir**: | |
| 98/2 | 108 |
| 95/5 | 108 |
| GMO/ethanol/isosorbid mononitrate: | |
| 58.8/39.2/2 | 84 |
| 57/38/5 | 81 |
| 54/36/10 | 32 |
| GMO/sodium fluoride**: | |
| 98/2 | 87 |
| 95/5 | 76 |
| GMO/prochlorperazin**: | |
| 98/2 | 78 |
| 95/5 | 90 |

*recovery was determined to be 79%
**the compositions were suspensions

The results show that all compositions tested have bioadhesive properties indicating that none of the active substances employed in the stated concentrations have a negative influence on the bioadhesiveness of the vehicle employed (with the exception of isosorbide mononitrate and dichlorphenac in relatively high concentrations). This observation indicates that the formation in situ of a fluid crystalline phase (most likely the cubic phase) is not significantly influenced by the active substances tested in the concentrations given above. A general working theory is that the establishment of a bioadhesion between a mucosal surface and a composition comprising a fatty acid ester with bioadhesive properties is dependent on a formation of a fluid crystalline phase in situ after in situ subjecting the composition to an aqueous medium. Most likely, the formation in situ of a cubic phase is responsible for the establishment of bioadhesion. Several factors may therefore influence the bioadhesiveness of a composition such as, e.g., the art and structure of the active substance, the physico-chemical properties of the active substance and the concentration of the active substance in the composition in question. If the concentration of the active substance becomes too high, the ability for forming a bioadhesive fluid crystalline phase of the composition may be negatively influenced.

Example 18

Investigation of the Influence of Different Excipients or Solvents on the Bioadhesiveness of GMO or GML Based Compositions The influence of various excipient and solvents were investigated. The various compositions were prepared as described above and the bioadhesiveness was tested using the test system No. 1. The following results were obtained:

| Composition % w/w | Bioadhesion Residual amount % |
|---|---|
| GMO[a] | 90 |
| GML[a] | 65* |
| GMO/GML[a] 40/60*** | 56* |
| Mixtures with solvents: | |
| GMO/water 85/15[b] | 94 |
| GML/ethanol 60/40 | 95** |
| GMO/ethanol/propylene glycol/water: | |
| 45/30/10/15 | 93 |
| Mixtures with solubilizing agents or preservatives: | |
| GMO/ethanol/benzylalcohol: | |
| 60/30/10 | 87** |
| GMO/ethanol/benzylalcohol/water: | |
| 60/20/5/15 | 80 |
| 50/20/10/20 | 89 |
| Mixtures with release modulating agents: | |
| GMO/ethanol/glycerol: | |
| 50/30/20 | 97 |
| GMO/ethanol/sesame oil: | |
| 59/40/1 | 96 |
| 58/40/2 | 93 |
| 50/40/10 | 14 |
| 50/30/20 | 0** |
| GMO/ethanol/soybean oil: | |
| 59/40/1 | 98 |
| 58/40/2 | 93 |
| 50/40/10 | 22 |
| 40/20/40 | 0** |
| GMO/ethanol/lecithin: | |
| 55/40/5 | 99 |
| 45/40/15 | 97 |

[a]melted gently before application
[b]lamellar phase
*lower results than expected; probably due to the reference values used in the analysis of the mixture
**test conditions as in Examples 1–13
***the GMO/GML mixture corresponds to about equal amounts of glycerol monooleate and glycerol monolinoleate The results given above show that addition of relevant excipients or solvents such as, e.g., agents which are known solubilizers for active substances or agents which are known as release modulating agent (i.e. agents which when added makes it possible to adjust or control the release of the active substance from a composition) does not significantly influence the bioadhesiveness of the composition when the agents (excipients or solvents) are added in relatively low concentrations (less than about 10% w/w). Thus, the release of an active substance from a composition which has proved to possess bioadhesive properties can be controlled by adjusting the amount of a release modulating agent such as, e.g., glycerol, sesame oil, soybean oil, lecithin, cholesterol etc.). Furthermore, if necessary, solubilisation of an active substance or a fatty acid ester for use in a bioadhesive composition can be effected by use of e.g. benzylalcohol without significantly influencing the bioadhesive properties of the composition. In conclusion, the bioadhesive principles according to the present invention have a high potential with respect to developing bioadhesive drug compositions having such a drug localization, such a drug release profile, and such a drug duration which are desirable or necessary under the given circumstances. Thus, the present inventors have found a very flexible principle for obtaining a bioadhesive drug delivery system.

Example 19

Investigation of the Presence of an Active Substance in a Fluid Crystalline Phase of GMO The present study was made in order to investigate whether incorporation of an active substance in a vehicle capable of forming a fluid crystalline phase also leads to incorporation of the active substance in the fluid crystalline phase.

Furthermore, the study was performed in order to examine the recovery of the samples applied.

A lipophilic (miconazole) and a hydrophilic active substance (lidocain hydrochloride), respectively, were applied on the rabbit jejunum test model for bioadhesiveness (test system No. 1). A vehicle of GMO/ethanol 60/40% w/w incorporating 2% w/w of either miconazole or lidocain hydrochloride was employed. The GMO/ethanol vehicle is bioadhesive in itself. After a flow period of 10 sec (corresponding to t=0), the sample applied is removed and analyzed for the content of the active substance applied. The experiment was repeated applying the same amount of the composition of GMO/ethanol/active substance but now the flow period was 30 minutes as usual (end of experiment).

As mentioned above, the samples were analyzed for the content of miconazole and lidocain hydrochloride, respectively. The following assays were employed:

Lidocain HCl

The content of lidocain HCl is determined by a HPLC method.

T: Dissolve the formulation in 30 ml methanol and transfer it quantitatively to a 50 ml volumetric flask. Add methanol to 50.00 ml.

R: Weigh out 100.00 mg lidocain HCl in a 100 ml volumetric flask. Dilute 1000 µl to 50.00 ml with mobile phase.

Analyse T and R on a suitable liquid chromatograph with UV-detector and integrator.

Column: Steel column, length 25 cm×4.6 mm i.d.
Stationary phase: Nucleosil C-18, 10 µm
Mobile phase: Methanol R: Acetic acid: Triethylamin: Water (50:1.5:0.5:48)
Flow: 1.5 ml/min
Temperature: Room temperature
Detection: 254 nm
Injection: 20 µl loop
Retention time: Lidocain HCl: about 3 min
Calculation:

$$\text{Lidocain HCL recovery, \%}: \frac{A_T \times n(g)}{A_R \times m(g) \times \% \text{ lidocain HCl}} \times 100\%$$

where
$A_T$ is the area of the test solution T;
$A_R$ is the area of the standard solution R;
n is the amount of standard weighed out (g);
m is the amount of formulation applied to the intestine (g);
% lidocain HCl is the content of lidocain HCl in the formulation determined as % w/w.

Miconazol

The content of miconazol is also determined by a HPLC method.

T: Dissolve the formulation in 30 ml methanol and transfer it quantitatively to a 50 ml volumetric flask. Add methanol to 50.00 ml.

R: Weigh out 100.00 mg miconazol in a 100 ml volumetric flask. Dilute 1000 µl to 50.00 ml with mobile phase.

Analyse T and R on a suitable liquid chromatograph with UV-detector and integrator.

Column: Steel column, length 25 cm×4.6 mm i.d.
Stationary phase: Spherisorb ODS 1, S5
Mobile phase: Methanol R: Buffer (85:15)
Flow: 1.0 ml/min
Temperature: 70° C.
Detection: 230 nm
Injection: 20 µl loop
Retention time: Miconazol: about 8 min
Buffer: 0.05 M $NH_4H_2PO_4$ (5.75 g in 1000 ml $H_2O$)
Calculation:

$$\text{Miconazol recovery, \%: } \frac{A_T \times n(g)}{A_R \times m(g) \times \% \text{ miconazol}} \times 100\%$$

where
- $A_T$ is the area of the test solution T;
- $A_R$ is the area of the standard solution R;
- n is the amount of standard weighed out (g);
- m is the amount of formulation applied to the intestine (g);
- % miconazol is the content of miconazol in the formulation determined as % w/w.

The results obtained are given below. In other experiments, both formulations applied were found to be bioadhesive by testing the residual amount of GMO. However, when the formulations are removed from the rabbit jejunum, there is a risk of loosing some of the active substance applied and the results given below should therefore be regarded as minimum values.

| Composition | Flow period | Recovery of active substance % mean of two determinations |
|---|---|---|
| GMO/ethanol/miconazole: | | |
| 58.8/39.2/2 | 10 sec | 85 |
| | 30 min | 93 |
| GMO/ethanol/lidocain HCl: | | |
| 58.8/39.2/2 | 10 sec | 37 |
| | 30 min | 7 |

The results show that the recovery of the lipophilic substance minonazole is almost 100%, irrespective of the flow period. This indicates that miconazole is incorporated in or surrounded by the fluid crystalline phase formed after subjecting the formulation to an aqueous medium by application of the formulation to the rabbit jejunum. Furthermore, it can be seen that miconazole only very slowly is released from the fluid crystalline phase formed in situ.

Lidocain hydrochloride is a hydrophilic substance. About 50% of the applied amount of active substance is released after the initial hydration of the rabbit jejunum (10 min) [i.e. at t=0] and almost all lidocaine hydrochloride is released after a flow period of 30 min. However, the low recovery of lidocain hydrochloride is most likely due to the fact that the active substance is freely water soluble. Thus, the lidocain hydrochloride is most likely also in this case incorporated in or surrounded by the fluid crystalline phase formed upon application of the formulation but the water solubility of lidocain hydrochloride is so high that it is quickly dissolved and released from the fluid crystalline phase.

In conclusion, the experiments reported above indicate that formulations in which GMO and an active substance is dissolved in ethanol serve as a precursor for the formation of an active substance containing fluid crystalline phase in situ, i.e. such formulations become bioadhesive in situ.

Example 20

Phase Transitions of GMO Containing Compositions

With respect to obtaining a composition which is bioadhesive in situ after application to skin or mucosa, a current working theory is that promising bioadhesive compositions comprising a bioadhesive fatty acid ester are those which are capable of acting as a precursor for the formation of a fluid crystalline phase in situ, i.e. the compositions should be capable of forming a fluid crystalline phase after subjecting or contacting the composition to the aqueous environment at the application site. Probably, it is the in situ formation of a cubic phase of the fatty acid ester which is responsible for an bioadhesive effect.

In the following tests are described which make it possible to determine the crystalline structure of suitable compositions for use according to the invention. The tests allows determination of the presence of, e.g., the GMO in a lamellar, hexagonal or cubic phase and it is possible to test the compositions before and after application to an appropriate application site. With respect to the presence of the various fluid crystalline phases in GMO or other glycerol fatty acid esters an excellent review is given by Ericsson et al. in ACS Symp. Ser. (1991), pp 251–265, American Chemical Society and by Larsson in Chapter 8 (part 8.2.1 entitled "Lamellar and hexagonal liquid-crystalline phases") in The Lipids Handbook edited by Gunstone et al. In short, the lamellar phase is the dominating one at a relatively low water content (below 20% w/w) and at a temperature of about 37° C., whereas the cubic phase dominates as the water content increases (more than about 200% w/w).

A. Phase Transition of GMO Compositions Determined by Differential Scanning Calorimetry (DSC)

The DSC measurements were performed using a Perkin Elmer Unix DSC model 7 Differential Scanning Calorimeter. The heating rate was 5° C./min and the scanning temperature was from 15° C. to 60° C. Samples were contained in sealed aluminium pans (Perkin Elmer No. B014-3017) and as a reference empty aluminium pans were employed. The phase transitions caused only a relatively small enthalpy change and, therefore, the amount of sample tested was optimized to about 30 mg.

The following compositions were tested:
1. GMO/water 85/15% w/w
2. GMO/water/lidocain base/lidocain HCl 62/33/1.7/3.3% w/w
3. GMO/water/lidocain base/lidocain HCl 62/33/2.5/2.5% w/w The results are given in FIGS. 3–5. DSC experiments give information of at which temperature a phase conversion takes place. DSC measurements alone give no information of the particular phases involved (e.g. lameller, cubic hexagonal etc.). However, if the DSC results as in the present case are compared with e.g. results from observation of the compositions in polarized light (see below under B) information on the crystalline phases as well as the transition temperature are obtained.

Figure 3:
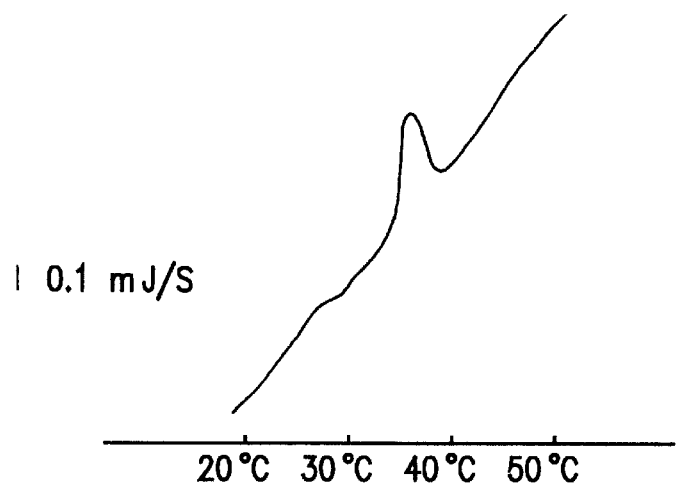
FIG. 3 shows a thermogram indicating the phase transition $L_\alpha$-to-Q (lamellar to cubic) for a GMO/water composition (85/15% w/w)

For composition No. 1, the results from the DSC and polarized light measurement show that the lamellar phase is present at room temperature and the lamellar phase is changed to the cubic phase when the temperature increases (FIG. 3). The transition temperature is about 37° C. For composition No. 2 the same picture as for composition No.

Figure 4:
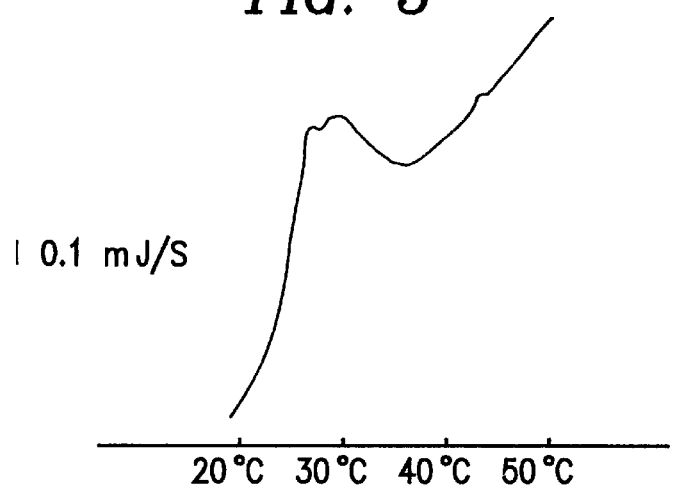
FIG. 4 shows a thermogram indicating the phase transition $L_\alpha$-to-Q (lamellar to cubic) for a GMO/water/lidocain base/lidocain hydrochloride composition (62/33/1.7/3.3% w/w)
Figure 5:
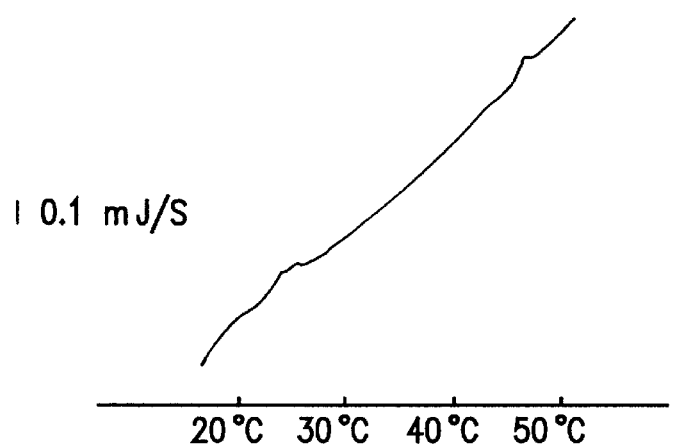
FIG. 5 shows a thermogram for a GMO/water/lidocain base/lidocain hydrochloride composition (62/33/2.5/2.5% w/w); the straight line indicates that no phase transition takes place

1 is observed (FIG. 4). The transition temperature in this case is about 30° C. For composition No. 3 another no phase conversion is observed (FIG. 5).

B. Phase Transition of GMO Compositions Determined by Polarimetry

Figure 6:
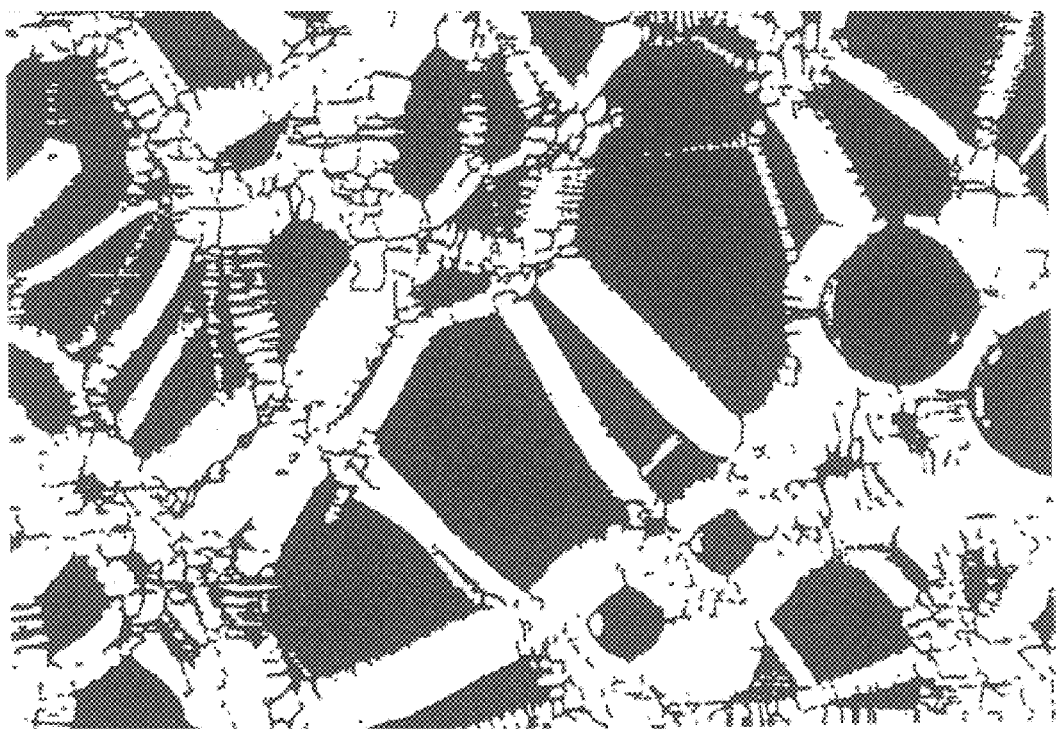
FIG. 6 shows a photograph of the lamellar phase of GMO as evidenced by polarized light. The appearance is like the structure of a pipe cleaner

The fluid crystalline phase can also be determined using polarized light and employing a stereomicroscope equipped with polarization filters. The appearance of reversed micelles (L2) are seen as a liquid oil, the lamellar phase ($L_\alpha$) is mucous-like and in polarized light it is birefringent. The appearance of the cubic phase is as a very viscous and glass-clear sample. In polarized light the cubic phase (Q) gives a black background with no details indicating that it does not reflect the light. The lamellar phase gives a structructe like a pipe cleaner on a black background (see FIG. 6) and the cubic phase gives different patterns but in most cases it resembles a mosaic like structure.

The method was employed in testing the phase behaviour of various bioadhesive compositions. The compositions were tested for crystalline phase after having been subjected to Test No. 1 for bioadhesiveness, i.e. the fluid crystalline phase formed was examined after application on rabbit jejunum and after subjecting the composition to an aqueous medium. The compositions tested contain the active substance in question dissolved in GMO/ethanol, i.e. no fluid crystalline phase is initially present.

The following compositions were tested:
1. GMO/ethanol 60/40% w/w
2. As composition No. 1 with 3% w/w estradiol
3. As composition No. 1 with 5% w/w indomethacin
4. As composition No. 1 with 10% w/w isosorbide mononitrate
5. GMO/miconazole 97/2% w/w
6. GMO/miconazole 92/8% w/w The compositions were removed immediately after testing in Test system No. 1 and the crystalline phase was examined in polarized light at room temperature. In all compositions the cubic phase had been formed. In composition No. 1 no crystal precipitation was observed. In composition No. 2, a crystals of estradiol had precipitated and it was observed that the crystals were contained within the fluid crystalline phase. In composition No. 3 precipitation of indomethacin crystals was observed after about 20 min. Furthermore, areas with the lamellar phase were also observed for composition No. 3. The fluid crystalline phase in the compositions Nos. 4–6 were also observed to be cubic. Other experiments have shown that composition No. 4 are only partly bioadhesive (residual amount when tested in test system No. 1 is about 30%) and in composition No. 6 a minor precipitation of crystals were observed.

In conclusion, compositions Nos. 1–3 and 5–6 have in other experiments proved to be bioadhesive. The results indicate that the cubic phase is formed irrespective of the presence of an active substance. The results may indicate that formation of a cubic phase is necessary to achieve bioadhesion, but no firm conclusion can be drawn. However, the results show that when a cubic phase is formed in situ then the composition is bioadhesive.

C. Phase Transition of GMO Compositions Determined by X-ray Diffraction

A modified diffraction thermal pattern (DTP) camera was employed. The source was an X-ray tube equipped with a Cu-anode emitting K$\alpha$-rays at a wavelength of 1.5418 Å. The X-ray generator was a Philips PW 1729.

The liquid crystalline state can be identified by low angle X-ray diffraction and its appearance in polarized light. The characteristic X-ray diffraction pattern for the three fluid crystalline ("fluid crystalline" is in the present context used synonymously with the term "liquid crystalline") (lamellar, hexagonal, cubic) will give rise to diffraction lines in the following orders:

1:1/2:1/1:4 . . . (lamellar)
1:1/√3:1/4:1/√7 . . . (hexagonal)
1:1/√2:1/√3:1/√4:1/√5:1/√6:1/√8 . . . (cubic)

In the case of the cubic form, the 2 different lattices will give rise to different diffraction lines.

The methods B and C were employed when testing the phase behaviour of various compositions. The compositions and results of the tests are given below.

The following compositions are precursors for the compositions tested. The precursor compositions are simple solutions and ethanol is used as a solvent. No water is contained in the precursor composition and therefore, no fluid crystalline phase is present.

Precursor compositions:
1. GMO/ethanol/miconazol 57/38/5% w/w
2. GMO/ethanol/lecithin 55/40/5% w/w
3. GMO/isosorbide mononitrate 97/3% w/w
4. GML/ethanol/lidocain base/lidocain HCl 57/38/2.5/2.5% w/w
5. GML/ethanol/lidocain base/lidocain HCl 58.2/38.8/1.5/1.5% w/w

| Composition | Determination of the liquid crystalline phase state by visual inspection by polarized light Temp. range 22→37° C. | Determination of the liquid crystalline phase state by X-ray diffraction Temp. range 22→37° C. | Temperature range | Spacings (Å) |
|---|---|---|---|---|
| GMO/water/miconazol 61.8/33.3/5 | lamellar → reversed hexagonal | mixture of lamellar/cubic → cubic (hexagonal II at 45° C.–>55° C.) | 15° C.–25° C. | 56.1 m, 48.9 w 34.2 w. diff. 28.8 w. diff. |
| | | | 25° C.–45° C. | 58.2 s, 46.7 m 33.2 w, 26.6 w |
| | | | 45° C.–>53° C. | 48.9 s, 29.1 m 25.1 m |
| GMO/water/lecithin 60/35/5 | cubic → cubic (few lipid crystals) | cubic → cubic | 15° C.–45° C. | 62.9 s, 54.1 w 38.5 w. diff. 32.5 w. diff. |
| | | | 45° C.–>55° C. | 62.9 s, 51.4 m 36.7 w, 29.7 w |

-continued

| Composition | Determination of the liquid crystalline phase state by visual inspection by polarized light Temp. range 22→37° C. | Determination of the liquid crystalline phase state by X-ray diffraction Temp. range 22→37° C. | Temperature range | Spacings (Å) |
|---|---|---|---|---|
| GMO/water/isosorbid mononitrat 63.7/34.3/2 | lamellar + cubic → cubic | cubic → cubic | 15° C.–27° C. | 65.5 s, 48.9 m 33.5 w. diff. |
| | | | 27° C.–50° C. | 60.5 s, 57.4 w 38.5 w. diff. 32.5 w. diff. |
| | | | 50° C.– | 62.9 s, 51.4 m 35.9 w, 29.9 w |
| GML/water/lidocain base/lidocain HCl 61.8/33.3/2.5/2.5 | | cubic → cubic with one crystal reflection | 15° C.–40° C. | 62.9 s, 51.4 w 36.3 w. diff. 30.5 w. diff. |
| | | | 40° C.–>55° C. | 96 s, 54 s. diff. |
| GML/water/lidocain base/lidocain HCl 63/34/1.5/1.5 | cubic → cubic | cubic → cubic | 20° C.–>52° C. | 61.7 s, 50.5 w 36.3 w. diff. 31.1 w. diff. |

Example 21

Study on the Bioadhesive Properties and Viscosities of Selected GMO-Containing Composition Disclosed in U.S. Pat. No. 5,262,164 (The Procter & Gamble Company) and of Elyzol® Dental Gel The present study was performed in order to examine whether the compositions disclosed in the above-mentioned US patent and the Elyzol® dental gel have bioadhesive properties. The compositions studied according to Procter & Gamble are disclosed in Examples I–III in U.S. Pat. No. 5,262,164.

The compositions tested had the following composition:

Compositions according to U.S. Pat. No. 5,262,164:

| Example I: | tetracycline hydrochloride | 49.9% w/w |
| | hydroxypropyl cellulose | 2.5% w/w |
| | glycerol monooleate | 47.6% w/w |
| Example II: | clindamycin phosphate | 35% w/w |
| | hydroxypropyl cellulose | 5% w/w |
| | lecithin | 25% w/w |
| | glycerol monooleate | 30% w/w |
| | polyethylene glycol 400 | 5% w/w |
| Example III: | metronidazole | 30% w/w |
| | hydroxypropyl cellulose | 5% w/w |
| | lecithin | 15% w/w |
| | glycerol monooleate | 30% w/w |

The results given below clearly show that none of the compositions tested have bioadhesive properties.

| Composition % w/w | Bioadhesion Visual evaluation | Viscosity shear rate 120 s$^{-1}$ temp. 20° C. |
|---|---|---|
| Example I of US 5,262,164* | 0 | 4400 |
| Example II of US 5,262,164* | 0 | >20,000 |
| Example III of US 5,262,164* | 0 | 4,000 |
| Elyzol ® dental gel | 0 | 2,100 |

*the composition were heated before application

Example 22

Dissolution Rate of Bioadhesive Compositions Containing Lidocain

The dissolution rate of lidocain from bioadhesive compositions comprising a mixture of lidocain base and lidocain hydrochloride was determined using Franz diffusion cells having a diffusion area of 1.77 cm$^2$. The study was run at a temperature of 37° C. and as diffusion membrane a cellulose membrane from Medicell International Ltd. was employed. The membrane employed has a pore size of about 2.4 nm and it retains particle having a molecular weight larger than about 12,000–14,000. Before application, the membrane was pretreated and thoroughly rinsed with distilled water. As receptor medium was used an isotonic 0.05M phosphate buffer pH 6.3 (Danish Drug Standards, DLS) and the medium was magnetically stirred at 300 rpm.

The cellulose membrane was allowed to equilibrate at 37° C. for 30 min in the receptor medium employed. After placing the membrane in the diffusion cell, an appropriate amount of the composition to be tested was applied by means of a syringe and care was taken to ensure a homogenous distribution of the composition on the total area of the membrane available for diffusion. Phosphate buffer was then loaded into the receptor part (time t=0) and at appropriate time intervals, samples of 1 ml were withdrawn and analyzed for content of lidocaine. The amount of receptor medium withdrawn was replaced with 1 ml fresh receptor medium. The HPLC method employed was the following:

| Mobile phase: | methanol:glacial acetic acid:triethylamine:water (50:1.5:0.5:48) whereto 20% v/v of water was added |
| Column: | Nucleosil C18, 10 μm, 25 cm, 4.6 mm i.d. |
| Column temperature: | room temperature |
| Flow: | 1.5 ml/min |
| Wavelength: | 254 nm |
| Sensitivity: | lowest detectable concentration corresponds to about 5 μg/ml |

The analysis was performed for the total amount of lidocain in the samples withdrawn (no discrimination between lidocain base and lidocain hydrochloride).

The composition tested was:

1. A composition containing GMO/water 65/35% w/w with a content of 1% w/w lidocain base and 1% w/w lidocaine hydrochloride 2. A composition containing GMO/water 65/35% w/w with a content of 3% w/w lidocain base and 3% w/w lidocaine hydrochloride
3. A composition containing GMO/water 65/35% w/w with a content of 5% w/w lidocain base and 5% w/w lidocaine hydrochloride The amount applied was about 350 mg.

The results are given below as the mean of two tests:

| Time | % w/w total lidocain dissolved Composition No. | | | |
|---|---|---|---|---|
| min | 1 | 2 | 2[a] | 3 |
| 2 | 0.59 | 0.64 | | 0.70 |
| 30 | 7.86 | 8.6 | 0.38 | |
| 33 | | | | 9.95 |
| 60 | 15.3 | 16.2 | 1.12 | |
| 66 | | | | 13.89 |
| 180 | 24.9 | 27.8 | 5.06 | |
| 183 | | | | 27.79 |
| 300 | 36.1 | 37.9 | 8.86 | 33.56 |
| 1440 | 62.6 | 71.3 | 30.29 | 58.7 |

[a]The composition No. 2 was tested as described above but instead of using a cellulose membrane a porcine buccal mucosa membrane was employed The results indicate that the release of lidocain from a GMO based vehicle is independent on the concentration of lidocain employed provided that the release takes place from a cubic phase system. Furthermore, the results indicate the capability of a GMO based vehicle to function as a drug delivery system (most likely a diffusion controlled drug delivery system).

With respect to the experiment involving a porcine buccal membrane, the results show as expected that the diffusion rate across the membrane is lowered compared with the dissolution rate measured over a cellulose membrane. The results give a clear indication of the potential of a bioadhesive composition containing a bioadhesive fatty acid ester as a drug delivery system.

Example 23

A Pilot Study of the Bioadhesive Properties of Glyceryl Mono-oleate (GMO) Over Time After Spray Application of a GMO/Ethanol Solution.

The aim of the study was to evaluate the bioadhesive properties of glyceryl mono-oleate (GMO) by estimating the recovery of GMO after oral spray administration. The study was designed as an open pilot study and 3 healthy Dumex employees participated in the study.

Study Materials

The spray applied was a composition of GMO/ethanol 60/40% w/w (Batch no. BDM 29). The mouth rinse was 20 ml of a 45% w/w aqueous solution of ethanol.

Methods

The solution was applied to the tongue and the buccal mucosa by spraying one puff on each location (a total of 3 puffs) corresponding to 250–300 mg of the solution. The amount of applied solution was determined by weighing the spray bottles before and after use.

After the solution was applied the test subjects were allowed to swallow (the GMO/ethanol and saliva). However, eating and drinking during the test periods were not allowed.

Samples were collected corresponding to t=0, 15, 30, 45, 60, 90 and 120 minutes (t=time after application). After the given time the mouth was rinsed. Two controls were made by rinsing the mouth with 45% aqueous ethanol and spraying the GMO-solution directly in the sample container. The collected samples were kept in a freezer at −18° C. until analyzed.

Pilot investigations have shown that a highly variable but acceptable recovery could be obtained upon mouth rinse for 15 seconds with 20 ml of 45% aqueous ethanol.

Assessments

The content of GMO in the samples was determined by the HPLC method described below.

The solution from the oral rinse was transferred to a 50 ml volumetric flask and 96% ethanol was added to a total volume of 50.00 ml. The test solutions are denoted T.

The standard solution, denoted R, was prepared by weighing out 100.00 mg glyceryl mono-oleate (GMO) in a 50 ml volumetric flask and adding methanol to a total volume of 50.00 ml.

T and R were analyzed on a suitable liquid chromatograph with UV-detector and integrator.

| Column: | Steel column, length 25 cm × 4.6 mm i.d. |
|---|---|
| Stationary phase: | Supelcosil LC-18 DM, 5 μm |
| Mobile phase: | Methanol R: Water: Buffer (840:120:40) |
| Flow: | 1.2 ml/min |
| Temperature: | Room temperature |
| Detection: | 214 nm |
| Injection: | 20 μl loop |
| Retention time: | GMO: about 24 min. |

Preparation of buffer solution:

Weigh out 13.33 g sodium acetate ($CH_3COONa, 3H_2O$) in a 1000 ml volumetric flask and dissolve in 500 ml of water. Add 5.8 ml of glacial acetic aid. Add water to 1000 ml. Adjust pH to 3.5 with hydrochloric acid (2 N).

The recovery of GMO was determined by the following calculation:

$$GMO \text{ recovery, } \% : \frac{A_T \times n(g) \times 100}{A_R \times m(g) \times \% \ GMO} \times 100\%$$

where: $A_T$ is the area of the test solution, $T$, $A_R$ is the area of the standard solution, $R$ $n$ is the amount of standard weighed out $(g)$, $m$ is the amount of applied solution $(g)$ found by weighing the spray bottle before and after use, $\% \ GMO$ is the content of $GMO$ in the solution determined as $\% \ w/w$.

Results 3 subjects participated (1 man, 2 women).

The study was conducted at Dumex A/S's facilities, Copenhagen, in week 2 1995.

Figure 7:
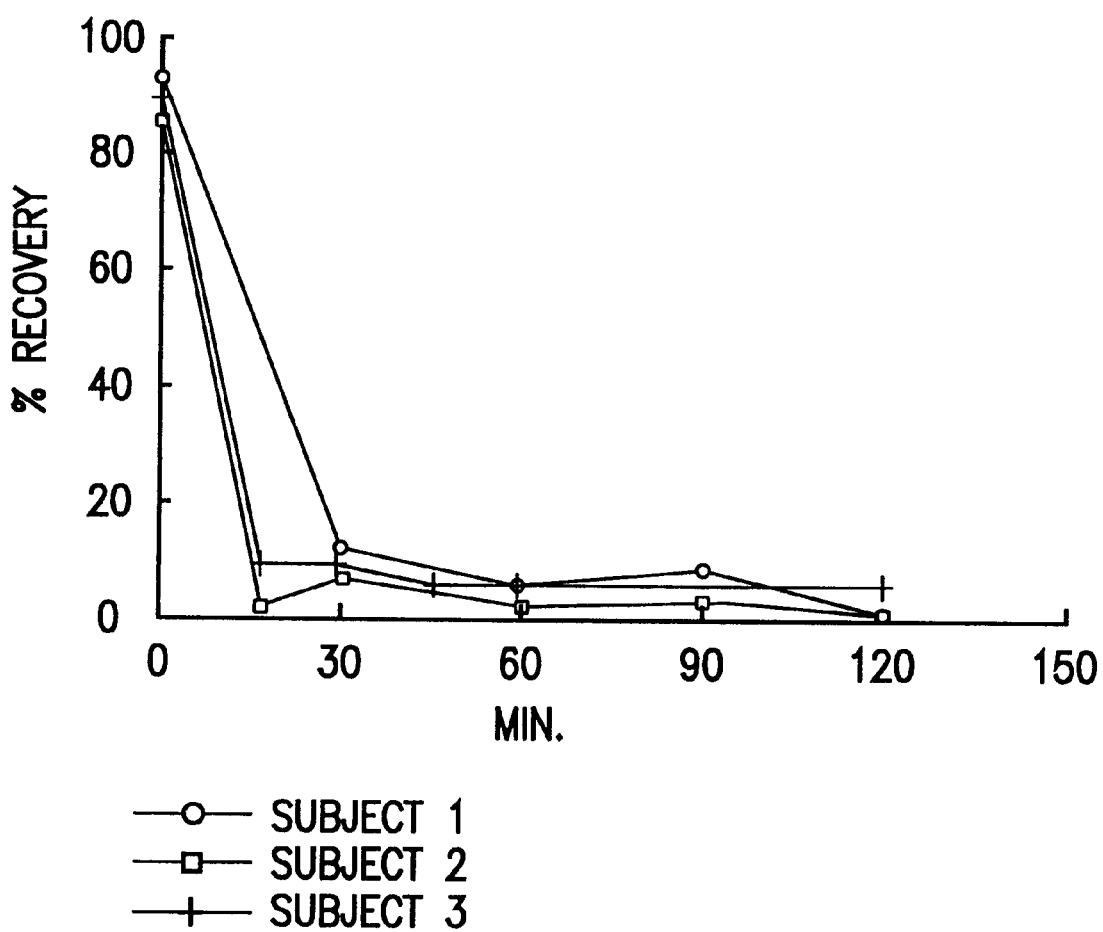
FIG. 7 shows the results from the study described in Example 23. The recovery of GMO is given against time after application; three subjects participated in the study

The results are given below in Table 1 and in FIG. 7.

TABLE 1

The amount of solution applied and the amount of GMO recovered after 0 to 120 minutes

| Time, min | Subject no. | Applied solution mg | Applied GMO, mg | GMO recovery mg | GMO recovery % |
|---|---|---|---|---|---|
| 0 min | 1 | 238.5 | 147.9 | 137.0 | 92.6 |
|  | 2 | 257.3 | 159.5 | 135.8 | 85.1 |
|  | 3 | 273.1 | 169.3 | 150.5 | 88.9 |
| 15 min | 1 | — | — | — | — |
|  | 2 | 250.9 | 155.6 | 5.2 | 3.3 |
|  | 3 | 287.2 | 178.1 | 20.3 | 11.4 |
| 30 min | 1 | 264.1 | 163.7 | 24.3 | 14.8 |
|  | 2 | 253.9 | 157.4 | 11.0 | 7.0 |
|  | 3 | 239.7 | 148.6 | 15.8 | 10.6 |
| 45 min | 1 | — | — | — | — |
|  | 2 | 247.4 | 153.4 | 7.0 | 4.6 |
|  | 3 | 274.7 | 170.3 | 10.0 | 5.9 |
| 60 min | 1 | 233.5 | 144.8 | 6.0 | 4.1 |
|  | 2 | 228.8 | 141.9 | 4.8 | 3.3 |
|  | 3 | 286.8 | 177.8 | 9.3 | 5.2 |
| 90 min | 1 | 246.1 | 152.6 | 14.4 | 9.5 |
|  | 2 | 268.4 | 166.4 | 6.1 | 3.7 |
|  | 3 | — | — | — | — |
| 120 min | 1 | 274.7 | 170.3 | 4.1 | 2.4 |
|  | 2 | 265.9 | 164.9 | 3.4 | 2.1 |
|  | 3 | 272.4 | 168.8 | 8.2 | 4.8 |
| ref. | control | 292.0 | 181.0 | 165.7 | 91.6 |
| ref. | control | 296.6 | 183.9 | 171.3 | 93.2 |

The recovery of GMO has decreased to approximately 10% after 15 minutes, followed by a very slow decline over the next hour to approx. 5%.

The results indicate that a major part of the composition applied had never had access to adhere to the oral mucosa. This is most likely due to the observation of an initial reaction of the composition with the saliva leading the composition to become greasy and then the greasy part of the composition is swallowed. However, the results from the time period t=15 min to t=120 min indicates that the amount of composition which in fact adheres to the oral mucosa nevertheless remains constant during this period.

What is claimed is:

1. A method of using fatty acid esters as bioadhesive substances for administering substances selected from the group consisting of active substances, protective substances, and mixtures thereof, the method comprising applying a bioadhesive composition to a portion of an animal or human body selected from the group consisting of oral, nasal, rectal, aural and vaginal mucosa, said bioadhesive composition comprising at least one substance selected from the group consisting of active substances, protective substances, and mixtures thereof, and at least 6% w/w, calculated on the composition, of at least one bioadhesive substance selected from the group consisting of fatty acid esters and mixtures of fatty acid esters.

2. A method according to claim 1, wherein the composition is applied to a mucosal site of the animal or human body at which it is subject to at least one of mechanical clearance or fluid clearance influence.

3. A method according to claim 1, wherein said bioadhesive composition is applied to one of a damaged or inflamed mucosa of the animal or human body.

4. A method according to claim 1, wherein the fatty acid component of the fatty acid ester is a fatty acid selected from the group consisting of a saturated and unsaturated fatty acid having a total number of carbon atoms of from $C_8$ to $C_{22}$.

5. A method according to claim 4, wherein the fatty acid component of said fatty acid ester is a saturated fatty acid moiety selected from the group consisting of caproic acid, caprylic acid, capric acid, lauric acid, myristic acid, palmitic acid, stearic acid, arachidic acid, and behenic acid.

6. A method according to claim 4, wherein the fatty acid component of said fatty acid ester is an unsaturated fatty acid moiety selected from the group consisting of palmitoleic acid, oleic acid, linoleic acid, linolenic acid, and arachidonic acid.

7. A method according to claim 1, wherein the fatty acid ester is selected from the group consisting of fatty acid esters of polyhydric alcohols, fatty acid esters of hydroxycarboxylic acids, fatty acid esters of monosaccharides, fatty acid esters of glycerylphosphate derivatives, fatty acid esters of glycerylsulfate derivatives, and mixtures thereof.

8. A method according to claim 7, wherein the polyhydric alcohol is selected from the group consisting of glycerol, 1,2-propanediol, 1,3-propanediol, diacylgalactosylglycerol, diacyldigalactosylglycerol, erythritol, xylitol, adonitol, arabitol, mannitol, and sorbitol.

9. A method according to claim 7, wherein the fatty acid ester is selected from the group consisting of glycerylmonooleate, glycerylmonolinoleate, glycerolmonolinolenate, and mixtures thereof.

10. A method according to claim 7, wherein the hydroxycarboxylic acid is selected from the group consisting of malic acid, tartaric acid, citric acid, and lactic acid.

11. A method according to claim 7, wherein the fatty acid ester is a fatty acid monoester of citric acid.

12. A method according to claim 7, wherein the monosaccharide is selected from the group consisting of glucose, mannose, fructose, threose, gulose, arabinose, ribose, erythrose, lyxose, galactose, sorbose, altrose, tallose, idose, rhamnose, and allose.

13. A method according to claim 7, wherein the fatty acid ester is a fatty acid monoester of a monosaccharide selected from the group consisting of sorbose, galactose, ribose, and rhamnose.

14. A method according to claim 7, wherein the glycerylphosphate derivative is a phospholipid selected from the group consisting of phospatidic acid, phosphatidylserine, phosphatidylethanolamine, phosphatidylcholine, phosphatidylglycerol, phosphatidylinositole, and diphosphatidylglycerol.

15. A method according to claim 7, wherein the fatty acid ester is a fatty acid ester of a glycerylphosphate derivative or a glycerylsulfate derivative, and the fatty acid component is selected from the group consisting of lauric acid, myristic acid, palmitic acid, stearic acid, oleic acid, linoleic acid, linolenic acid, and behenic acid.

16. A method according to claim 7, wherein the fatty acid ester is selected form the group consisting of dioleoyl phosphatidylcholin, dilauroyl phosphatidylcholin, dimyristoyl phosphatidylcholin, dipalmitoyl phosphatidylcholin, distearoyl phosphatidylcholin, dibehenoyl phosphatidylcholin, dimyristoyl phosphatidylethanolamine, dipalmitoyl phosphatidylethanolamine, dioleoyl phosphatidylglycerol, dilauroyl phosphatidylglycerol, dimyristoyl phosphatidylglycerol, dipalmitoyl phosphatidylglycerol, distearoyl phosphatidylglycerol, dipalmitoyl phosphatidic acid and mixtures thereof.

17. A method according to claim 1, wherein said fatty acid ester or mixture of fatty acid esters forms a fluid crystalline phase when contacted with an aqueous medium.

18. A method according to claim 1, wherein the composition is adapted for use as one of a pharmaceutical, cosmetic, veterinary, or agrochemical composition.

19. A method according to claim 1, wherein said fatty acid ester or mixture of fatty acid esters is present in a concentration of at least about 15% w/w, calculated on the composition.

20. A method according to claim 1, wherein said fatty acid ester or mixture of fatty acid esters is present in a concentration of at the most 95% w/w, calculated on the composition.

21. A method according to claim 1, wherein said fatty acid ester or mixture of fatty acid esters is present in a concentration of at the most 80% w/w, calculated on the composition.

22. A method according to claim 1, wherein contact of the composition with an aqueous medium results in formation of a fluid crystalline phase.

23. A method according to claim 1, wherein the composition further comprises a pharmaceutically acceptable excipient.

24. A method according to claim 1, wherein the composition is in the form of a spray.

* * * * *